US012735413B2

(12) United States Patent
Borsari et al.

(10) Patent No.: US 12,735,413 B2
(45) Date of Patent: Sep. 15, 2026

(54) TRIAZINE DERIVATIVE AS REVERSIBLE AND IRREVERSIBLE COVALENT INHIBITORS OF PI3K

(71) Applicant: UNIVERSITÄT BASEL, Basel (CH)

(72) Inventors: Chiara Borsari, Basel (CH); Matthias Wymann, Bern (CH)

(73) Assignee: UNIVERSITÄT BASEL, Basel (CH)

( * ) Notice: Subject to any disclaimer, the term of this patent is extended or adjusted under 35 U.S.C. 154(b) by 384 days.

(21) Appl. No.: 18/554,474

(22) PCT Filed: Apr. 9, 2022

(86) PCT No.: PCT/EP2022/059549
§ 371 (c)(1),
(2) Date: Oct. 8, 2023

(87) PCT Pub. No.: WO2022/214702
PCT Pub. Date: Oct. 13, 2022

(65) Prior Publication Data

US 2024/0208957 A1 Jun. 27, 2024

(30) Foreign Application Priority Data

Apr. 9, 2021 (EP) .................................... 21167750
Sep. 23, 2021 (EP) .................................... 21198539

(51) Int. Cl.
*C07D 413/14* (2006.01)
*A61K 31/5377* (2006.01)
(Continued)

(52) U.S. Cl.
CPC ........ *C07D 413/14* (2013.01); *A61K 31/5377* (2013.01); *A61P 35/02* (2018.01); *C07D 401/14* (2013.01); *C07D 403/14* (2013.01)

(58) Field of Classification Search
CPC ................ C07D 413/14; C07D 401/14; C07D 403/14; A61K 31/5377; A61K 31/53; A61P 35/00; A61P 37/00; A61P 35/02
(Continued)

(56) References Cited

U.S. PATENT DOCUMENTS 5,922,820 A 7/1999 Share
2011/0230476 A1 9/2011 Niu et al.

FOREIGN PATENT DOCUMENTS

JP 2012508223 4/2012
JP 2019519507 7/2019
(Continued)

OTHER PUBLICATIONS

Nacht Mariana et al, "Discovery of a Potent and Isoform-Selective Targeted Covalent Inhibitor of the Lipid Kinase PI3K[alpha]", Journal of Medicinal Chemistry, vol. 56, No. 3, Feb. 14, 2013 (Feb. 14, 2013), p. 712-721.

*Primary Examiner* — Taylor V Oh
(74) *Attorney, Agent, or Firm* — JMB Davis Ben-David

(57) ABSTRACT

Our invention relates to novel triazine compounds, containing chemical reactive groups (warheads) and behaving as reversible and irreversible covalent inhibitors. Linkers have been introduced to target a solvent exposed, distal cysteine at >10 Å from the core reversible inhibitor. Different exit vectors have been investigated to modulate inhibitor intrinsic reactivity and efficiency in covalent bond formation. We disclose novel, optimized covalent modifiers of phosphoinositide 3-kinase alpha (PI3Kα), an enzyme frequently altered in human malignancies. The compounds of the invention could be exploited as therapeutic agents and chemical probes useful for the investigation of the role of PI3K isoforms in cancer and metabolism, and for treatment of PI3Kα-driven cancers and malformations.

15 Claims, 1 Drawing Sheet

(51) Int. Cl.
*A61P 35/02* (2006.01)
*C07D 401/14* (2006.01)
*C07D 403/14* (2006.01)

(58) Field of Classification Search
USPC .................................................... 514/210.18
See application file for complete search history.

(56) References Cited

FOREIGN PATENT DOCUMENTS

| | | |
|---|---|---|
| WO | 2010052569 | 5/2010 |
| WO | 2012101654 | 8/2012 |
| WO | 2017198346 | 11/2017 |
| WO | 2018009638 | 1/2018 |

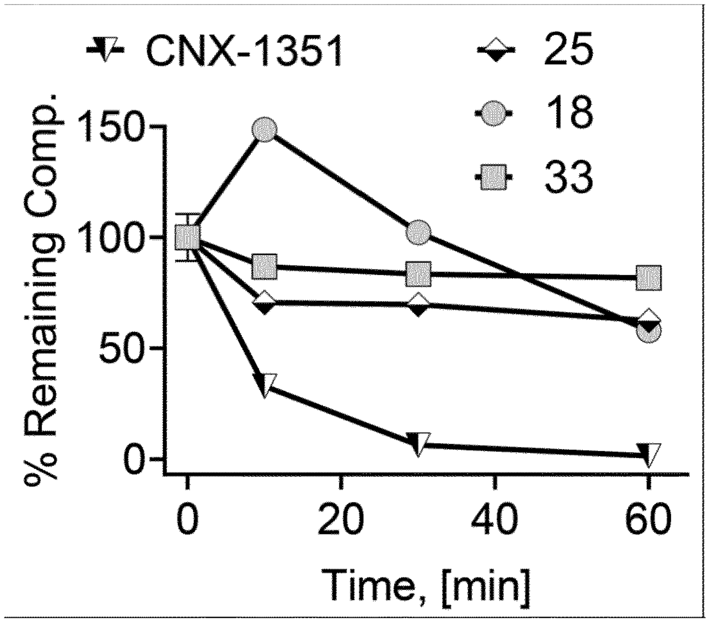
CNX-1351
25
18
33
% Remaining Comp.
150
100
50
0
0
20
40
60
Time, [min]

TRIAZINE DERIVATIVE AS REVERSIBLE AND IRREVERSIBLE COVALENT INHIBITORS OF PI3K

CROSS-REFERENCE TO RELATED APPLICATIONS

This is the U.S. National Stage of International Patent Application No. PCT/EP2022/059549, filed Apr. 9, 2022, which claims the benefit of European Patent application No. 21167750.5, filed Apr. 9, 2021 and European Patent Application No. 21198539.5, filed Sep. 23, 2021.

FIELD OF THE INVENTION

The invention relates to novel triazine compounds, containing chemical reactive groups (warheads), as therapeutic agents and chemical probes useful for modulating cellular activities such as signal transduction, proliferation, differentiation and cell death. The compounds of the invention modulate kinase activity, in particular that of phosphoinositide 3-kinase (PI3K).

BACKGROUND OF THE INVENTION

Protein kinases participate in the signaling events and control cellular activation, growth, differentiation, survival and migration in response to extracellular mediators or stimuli including growth factors, cytokines or chemokines.

Increased protein kinase activities are involved in many diseases including cancer, inflammatory disorders, metabolic and immunological diseases. These can be caused either directly or indirectly by the failure of control mechanisms due to mutation(s), overexpression or inappropriate control of enzyme activity.

The phosphoinositide 3-kinase (PI3K) signaling pathway plays a key role in many cellular processes, including cell growth, proliferation and survival. The PI3K family is divided into three classes according to their amino acid sequences, homology and substrate specificity. Class I PI3Ks are activated downstream of cell surface receptors, including receptor protein tyrosine kinases (RTKs), G-protein-coupled receptors (GPCRs) and immunoglobulin receptors. Class IA PI3Ks are obligate heterodimers composed of a catalytic subunit (p110α, p110β, or p110δ) and an associated regulatory subunit (p85α, p85β, p50α, p55α, or p55γ). The class IB PI3Kγ operates downstream of GPCRs and consists of a catalytic subunit (p110γ) and an adapter subunit (p84 or p101). Cell surface receptors activate PI3K to produce PtdIns(3,4,5)$P_3$, which serves as a docking site for protein kinase B (PKB/Akt) and 3-phosphoinositide-dependent protein kinase 1 (PDK1). This results in phosphorylation of the kinase domain at two regulatory sites, Thr308 by PDK1 and Ser473 by mTOR complex 2 (mTORC2). Hyperactivation of the PI3K/mTOR pathway can occur at multiple levels of this signaling cascade, finally promoting cancer growth and progression. Loss or inactivation of the tumor suppressor Phosphatase and Tensin homolog (PTEN), mutation or amplification of cell surface receptors, as well as the presence of activating hotspot mutations in PIK3CA, play a key role in human carcinogenesis. In addition, overactivation of the PI3K/mTOR axis has been associated with resistance to multiple cancer treatments. Therefore, PI3K inhibitors are considered as valuable asset in cancer therapy.

A considerable effort has been dedicated to the development of drugs targeting PI3K signaling, and many of them are currently being evaluated in clinical trials. Selective PI3Kα inhibitors could be beneficial for PIK3CA-mutant tumors and PIK3CA-related overgrowth syndromes (PROS), minimizing on-target metabolic side effects of pan-PI3K inhibitors. BYL719/ Alpelisib/PIKRAY from Novartis and GDC-0032/Taselisib from Genentech act as a reversible modifier and are claimed as PI3Kα selective inhibitors. However, at the concentration needed for in vivo experiments they are not able to discriminate between PI3K isoforms. Only one PI3Kα covalent inhibitor is currently available, dubbed CNX-1351, but it shows a limited in vitro and cellular potency, low aqueous solubility and metabolic instability.

The patent application describes certain triazine derivatives having PI3K inhibitory activity and acting as irreversible covalent and reversible covalent modifiers, and their use as pharmaceuticals. The compounds herein covered have significant advantages in terms of potency, metabolic stability, and drug-likeness properties as compared to CNX-1351. In addition, the patent application describes linkers for the development of covalent kinase inhibitors.

SUMMARY OF THE INVENTION

The invention relates to new triazine-based compounds acting as irreversible modifiers and their use as therapeutic agents and chemical probes.

A first aspect of the inventio relates to a compound of formula (IV), particularly of formula (IVa), or a prodrug, metabolite, tautomer, solvate or pharmaceutically acceptable salt thereof, (IV)

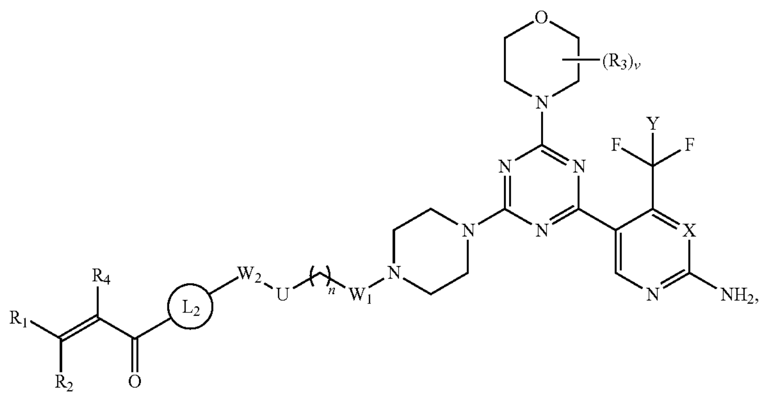

-continued (IVa)

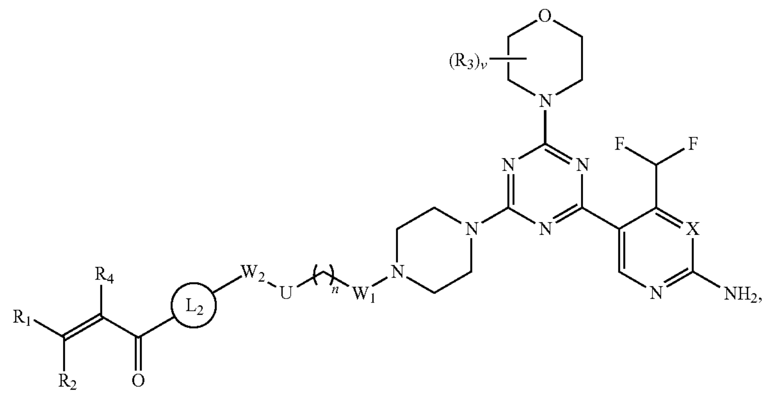

wherein

X is CH or N,

Y is H or F, $R_1$ and $R_2$ are independently of each other selected from H, $CH_3$, cyclopropyl, —F, —$CH_2$—F, —$CH_2$—$CH_2$—F, —CN,

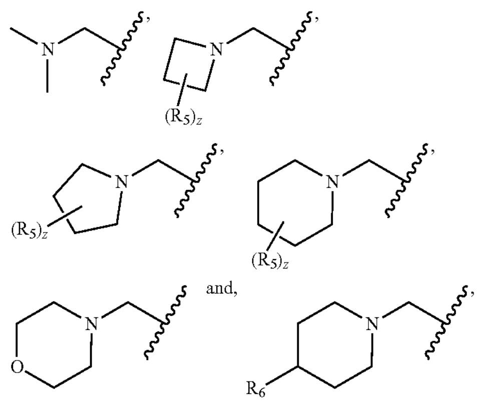

and, with $R_5$ being F or $CH_3$, $R_6$ being $C_{1-6}$-alkyl and z being 0, 1 or 2, $R_3$ is $C_{1-3}$-alkyl or two residues $R_3$ form a bridge —$(CH_2)_r$— with r being 1, 2 or 3, v is 0, 1, 2, 3 or 4, $R_4$ is H, F or —CN, $L_2$ is a moiety selected from

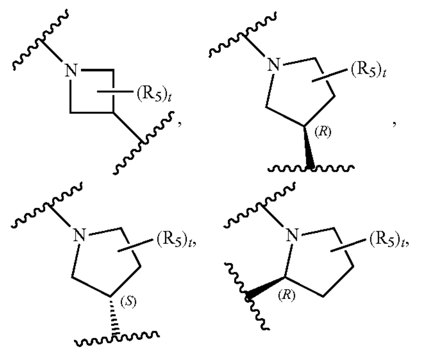

-continued

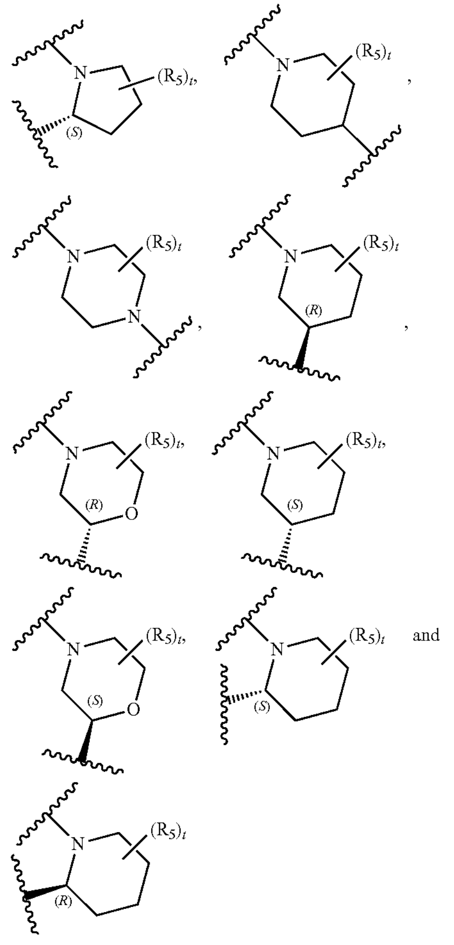

and with $R_5$ being $C_{1-3}$-alkyl, F, —$CH_2$CN or —CN and t being 0, 1 or 2, $W_1$ is CO or $CH_2$, $W_2$ is selected from O, $CH_2$ and CO, U is selected from O, $CH_2$, CO, NH, and $N(CH_3)$, n is 1 or 2.

A second aspect of the invention relates to the compound according to the first aspect of the invention for use in the treatment of a disease.

A third aspect of the invention relates to the compound according to the first aspect of the invention for use in the treatment of tumor disease, overgrowth syndrome, neurological disease disorder, immunological disease disorder.

A fourth aspect of the invention relates to an intermediate of formula (VI), (VI)

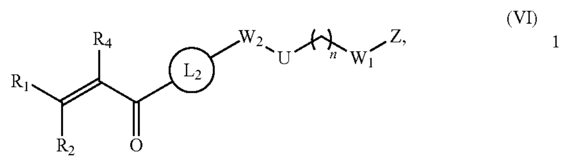

wherein $R_1$, $R_2$, $R_4$, $L_2$, $W_2$, U, n and $W_1$ are defined as described above, Z is —OH, Br, COOH, —C(OH)$NH_2$.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials herein described.

Definitions

The term "alkyl" as used herein refers to a saturated linear-chain monovalent hydrocarbon group of one to five carbon atoms ($C_1$-$C_5$). Examples of alkyl groups include, but are not limited to, methyl, ethyl, 1-propyl (n-propyl), 1-butyl (n-butyl).

The terms "heterocycle", "heterocyclyl" and "heterocyclic ring" are used interchangeably herein and refer to a saturated or unsaturated carbocyclic radical of 4 to 6 ring atoms in which at least one ring atom is a heteroatom, particularly nitrogen, and the remaining ring atoms being carbon atoms, wherein one or more ring atoms are optionally substituted independently with one or more substituents, particularly selected from —$CH_3$ and —F.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images 5 of one another.

Stereochemical definitions and conventions used herein generally follow S. P. Parker, Ed., McRaw-Hiff Dictionary of Chemical Terms (1984), McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes R and S, are used to denote the absolute configuration of the molecule about its chiral center(s). For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate. The term "tautomer" or "tautomeric form" refers to structural isomers of different energies, which are interconvertible via a low energy barrier. For example, proton tautomers include interconversions via migration of a proton, such as ketoenol and imine-enamine isomerizations.

The term "enone" refers to a $\alpha,\beta$-unsaturated carbonyl, that is a type of organic compound consisting of an alkene conjugated to a ketone. The simplest enone is methyl vinyl ketone (butenone) or $CH_2$=$CHCOCH_3$. They are electrophilic at both the carbonyl carbon as well as the β-carbon. Depending on conditions, either site is attacked by nucleophiles. Additions to the alkene are called Michael additions and are used in the present invention to covalently modify Cysteine 862 in PI3Kα.

The term "acrylamide" refers to an amide that is derived from acrylic acid and has the general chemical formula $CH_2$=CHC(O)$NH_2$. Acrylamides are used in compounds of the present invention and undergo Michael addition with Cysteine 862 in PI3Kα.

The term "PI3K" refers to phosphoinositide 3-kinase.

The term "PI3Kalpha", "PI3Kα" or "p110a protein" relates to a subunit of PI3K that is encoded by the PI3KCA gene.

The term "irreversible" or "irreversible inhibitor" refers to an inhibitor that is able to be covalently bonded to a PI3 kinase in a substantially non- reversible manner, whereas a reversible inhibitor is able to bind to (but is generally unable to form a covalent bond with) a kinase, and therefore can be dissociated from the PI3 kinase. An irreversible inhibitor will remain substantially bound to a kinase once covalent bond formation has occurred. Methods for identifying if a compound is acting as an irreversible inhibitor are known to one of ordinary skill in the art. Such methods include, but are not limited to, enzyme kinetic analysis of the inhibition profile of the compound with the kinase, the use of mass spectrometry of the protein drug target modified in the presence of the inhibitor compound, the use of X-ray crystallography to solve the complex between the protein drug target and the inhibitor compound, discontinuous exposure, also known as "washout" experiments, as well as other methods known to one of skill in the art.

The term "reversible covalent" refers to an inhibitor that covalently modify a targeted cysteine, however the free energy difference separating the noncovalently-bonded reactants from bonded product is near equilibrium and the activation barrier is relatively low such that the reverse reaction which cleaves the chemical bond easily occurs (examples include nitrile-based reversible covalent inhibitors).

The term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein. Warhead groups are essential for covalently, and irreversibly, inhibiting the protein.

The term "inhibitor" is defined as a compound that binds to and inhibits PI3 kinase with measurable affinity. In certain embodiments, the inhibitors are characterized by $IC_{50}$ and/or rate constant for irreversible inactivation ($K_{inact}$).

The term "CNX-1351" refers to 1-[4-[[2-(1H-indazol-4-yl)-4-(4-morpholinyl)thieno[3,2-d]pyrimidin-6-yl]methyl]-1-piperazinyl]-6-methyl-5-heptene-1,4-dione (CAS 1276105-89-5).

The phrase "pharmaceutically acceptable salt" as used herein, refers to pharmaceutically acceptable organic or inorganic salts of a compound of the invention. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, tert-butoxycarbonyl (BOC), benzyloxycarbonyl and 9-fluorenylmethylenoxycarbonyl (Fmoc). For a general description of protecting groups and their use, see T. W. Greene, Protective Groups in Organic Synthesis, John Wiley & Sons, New York, 1991.

The terms "compound of this invention" and "compounds of the present invention" and "compounds of formula (I, II, III)" include stereoisomers, geometric isomers, tautomers, solvates, pharmaceutically acceptable salts, and solvates of the salts thereof.

DETAILED DESCRIPTION

The invention relates to novel triazine-based compounds acting as reversible or irreversible modifiers of PI3 kinase, particularly PI3Kα, and their use as therapeutic agents and chemical probes.

Compounds of the present invention have higher aqueous solubility (>30-fold), higher potency in vitro and in cell (>7-fold), and higher metabolic stability compared to the known inhibitor CNX-1351.

An important aspect of the invention relates to superior reaction parameters in preferred molecules (particularly inhibitors characterized by a warhead that forms an acrylamide moiety) that result in a highly selective target engagement and reduced or negligible off-target reactivity:

i) the on-target reaction of the covalent inhibitors is defined by the inhibitor dissociation constant $K_i$, which described the reversible equilibrium of enzyme (E) and inhibitor (I) complex formation $$E+I \leftarrow\rightarrow E\sim I$$

and $K_{inact}$, which defines the reaction rate of covalent bond formation between inhibitor and enzyme to form the covalent inhibitor-enzyme complex (EI):

$$E\sim I \rightarrow EI$$

ii) off-target reactions with ubiquitous sulfhydryls (S) and other nucleophils present in physiologic environments such as cells and body fluids are driven by the intrinsic reactivity of the warhead that is defined by $K_{chem}$ driving the conversion of S and I to form the sulfhydryl-adduct (SI)

$$S+I \rightarrow SI$$

High intrinsic warhead reactivity (high $K_{chem}$ values) leads to the formation of unwanted sulfhydryl-adducts resulting in loss of compound, covalent modification of cellular components, toxicity and anti-compound immune reactions:

As illustrated in Table 1 preferred molecules show a low $K_{chem}$, low $K_i$, high $K_{inact}$, a high $K_{inact}/K_i$ ratio to warrant superior on-versus off target engagement.

A first aspect of the inventio relates to a compound of formula (IV), particularly of formula (IVa), or a prodrug, metabolite, tautomer, solvate or pharmaceutically acceptable salt thereof, particularly a tautomer, solvate or pharmaceutically acceptable salt thereof, (IV)

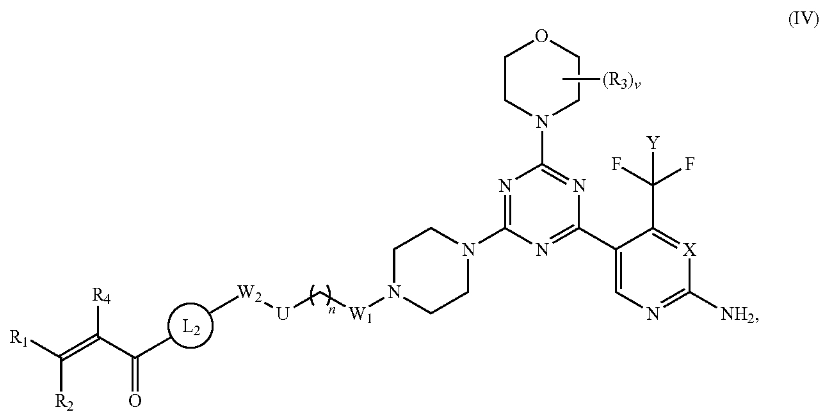

-continued (IVa)

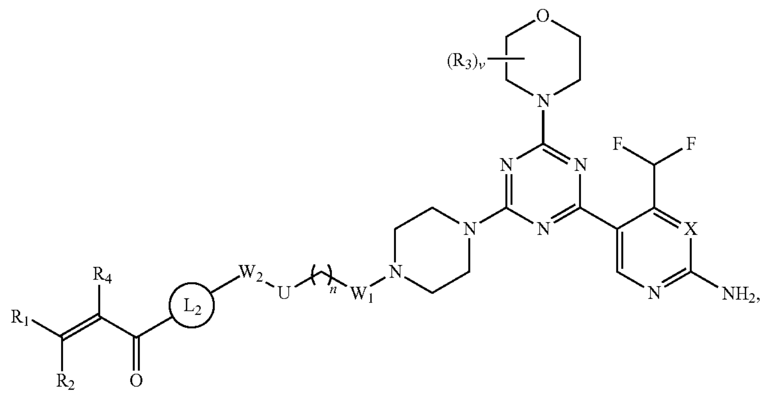

wherein

X is CH or N, particularly N,

Y is H or F, particularly H, $R_1$ and $R_2$ are independently of each other selected from H, $CH_3$, cyclopropyl, —F, —$CH_2$—F, —$CH_2$—$CH_2$—F, —CN,

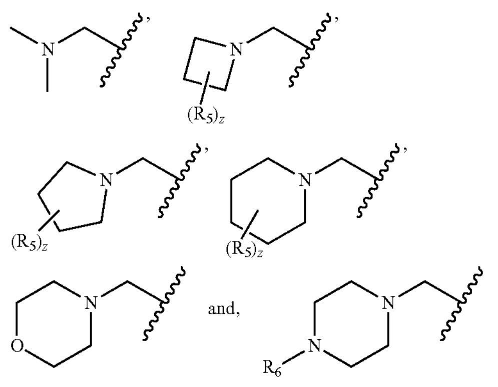

and, with $R_5$ being F or $CH_3$, $R_6$ being $C_{1-8}$-alkyl and z being 0, 1 or 2, $R_3$ is $C_{1-3}$-alkyl or two residues $R_3$ form a bridge —$(CH_2)_r$— with r being 1, 2 or 3, particularly with r being 1 or 2, v is 0, 1, 2, 3 or 4, $R_4$ is H, F or —CN, $L_2$ is a moiety selected from

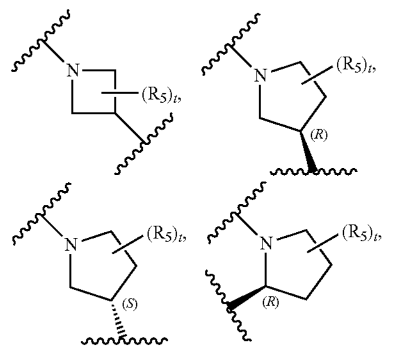

-continued

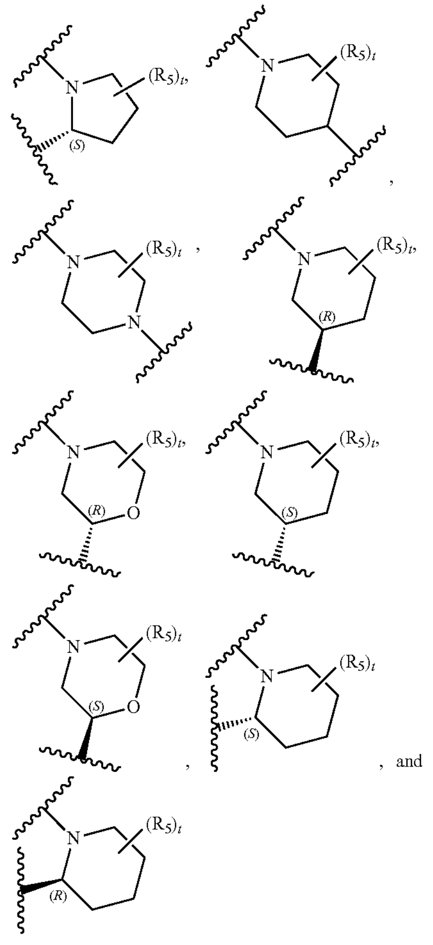

, and with $R_5$ being $C_{1-3}$-alkyl, F, —$CH_2CN$ or —CN and t being 0, 1 or 2, $W_1$ is CO or $CH_2$, $W_2$ is selected from O, $CH_2$ and CO, U is selected from O, $CH_2$, CO, NH, and $N(CH_3)$, particularly O, $CH_2$, NH, and $N(CH_3)$, n is 1 or 2.

An inhibitor according to the present invention comprises a multi-cyclic scaffold and a so-called warhead that is connected to the scaffold via a linker. The scaffold comprises a triazine moiety that is substituted by three heterocycles, namely a morpholinyl, a piperazinyl and a pyridinyl or pyrimidinyl moiety. The pyridinyl or pyrimidinyl moiety is substituted by a fluorinated methyl and an amine moiety.

The morpholinyl moiety is optionally substituted. The piperazinyl is bound to the linker which is composed of $L_2$, $W_2$, U, $C_{1-2}$-alkyl and $W_1$.

The molecules present certain reactive functional groups so called "warheads." As used herein, the term "warhead" or "warhead group" refers to a functional group present on a compound of the present invention wherein that functional group is capable of covalently binding to an amino acid residue (such as cysteine, lysine, histidine, or other residues capable of being covalently modified) present in the binding pocket of the target protein, thereby irreversibly inhibiting the protein.

The inhibitors according to the present invention may bind covalently to Cys862 of PI3Kα. Such inhibitors are characterized by a carbon-carbon double bond in the warhead. The stability of the bond may be modulated by substituents $R_1$, $R_2$ and $R_4$ to achieve inhibitors that form a stable covalent bond or a reversible covalent bond.

The compounds disclosed herein show a good PI3 kinase inhibition, particularly a good PI3Kα inhibition, in combination with a good stability.

In certain embodiments, $R_1$ is H, $CH_3$ or —$CH_2F$.

In certain embodiments, $R_2$ is H or cyclopropyl.

In certain embodiments, $R_2$ is cyclopropyl and $R_4$ is —CN.

In certain embodiments, $R_3$ is a $C_{1-3}$-alkyl, particularly $CH_3$.

In certain embodiments, v is 0, 1 or 2, more particularly 0 or 1.

In certain embodiments, the compound is a compound of formula (V), particularly (Va), (V)

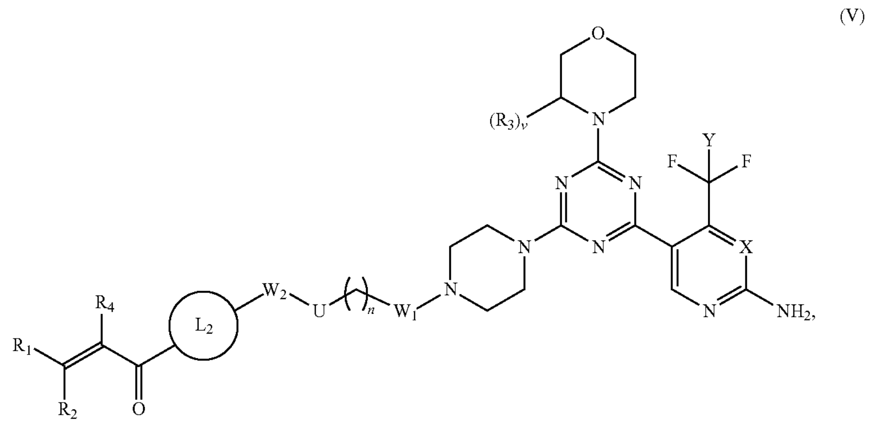

(Va)

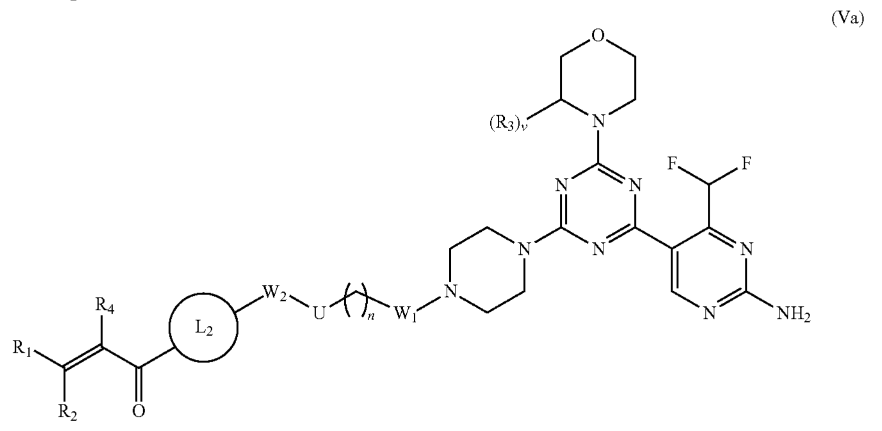

wherein

X, Y, $R_1$, $R_2$, $R_3$, $R_4$, $W_1$, n, U, $W_2$, $L_2$ are defined as described above, v is 0 or 1.

In certain embodiments, the compound according to the first aspect of the invention is a compound of formula (I) or (II), (I)

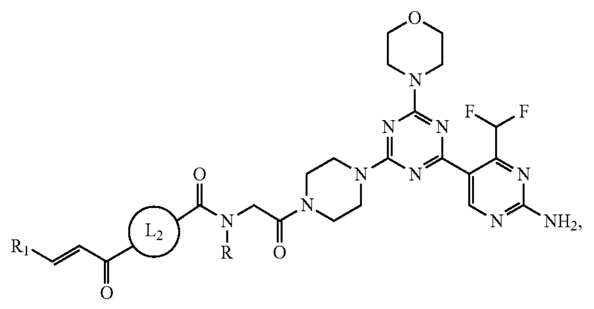

Wherein

R is H or $CH_3$, $R_1$ is H or $CH_3$,

L$_2$ is a moiety selected from
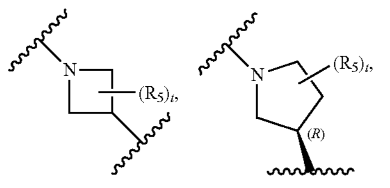
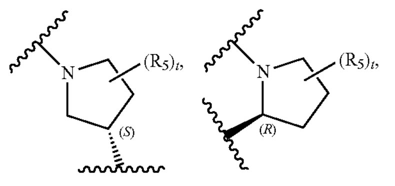
-continued
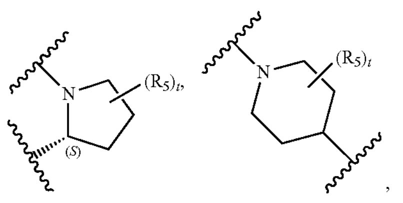
,
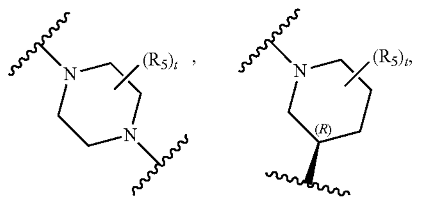
-continued
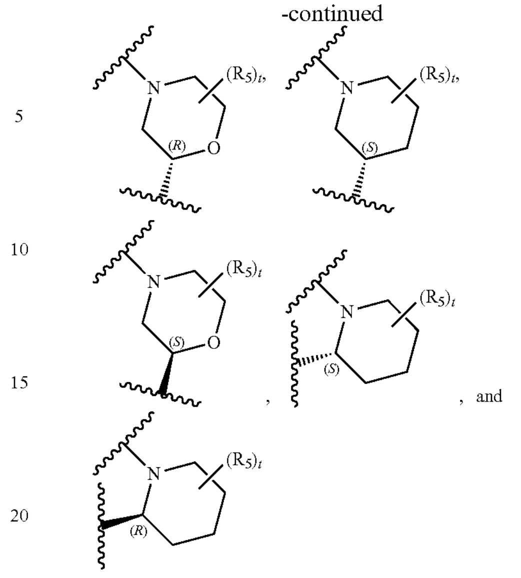
, , and
with $R_5$ being $C_{1-3}$-alkyl, F, —$CH_2$CN or —CN and t being 0, 1 or 2,
(II)
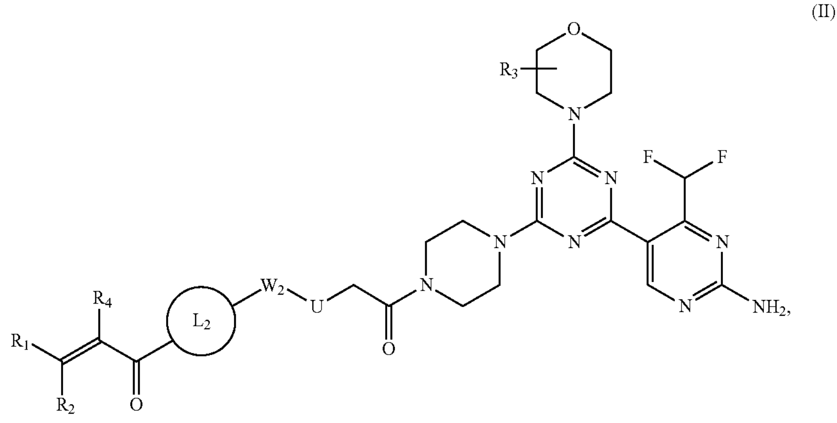
Wherein
$R_3$ is H or $CH_3$
L$_2$ is a moiety selected from
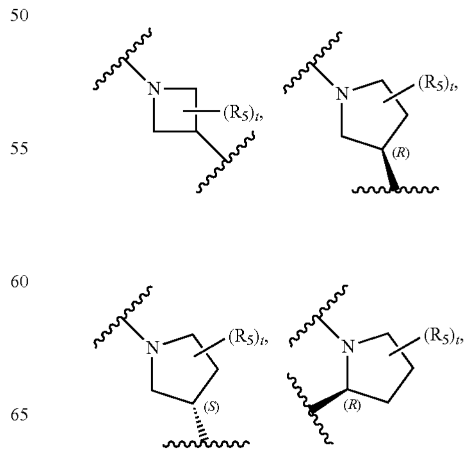

-continued

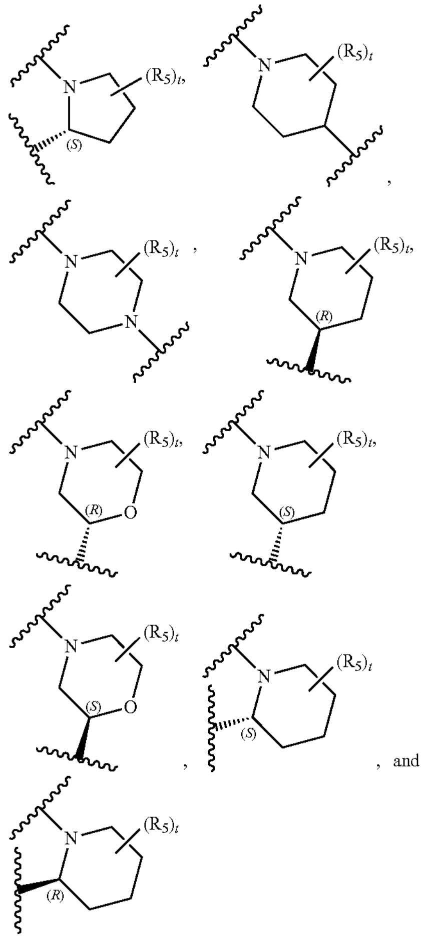

, , , , and with $R_5$ being $C_{1-3}$-alkyl, F, —$CH_2CN$ or —CN and t being 0, 1 or 2

$W_2$ is O when U is $CH_2$, or $W_2$ is $CH_2$ when U is O;

U is O when $W_2$ is $CH_2$, or U is $CH_2$ when $W_2$ is O;

$R_1$ is H or —$CH_2$—F, $R_2$ is H or cyclopropyl, $R_4$ is H or F, and reversible analogs, prodrugs, metabolites, tautomers, solvates and pharmaceutically acceptable salts thereof (I, II).

In certain embodiments, the compound according to the first aspect of the invention is a compound of formula (la),( (Ia)

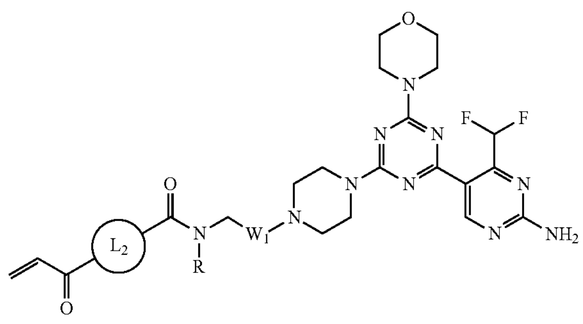

wherein

R is H or $CH_3$;

$W_1$ is CO and $CH_2$;

$L_2$ is a moiety selected from

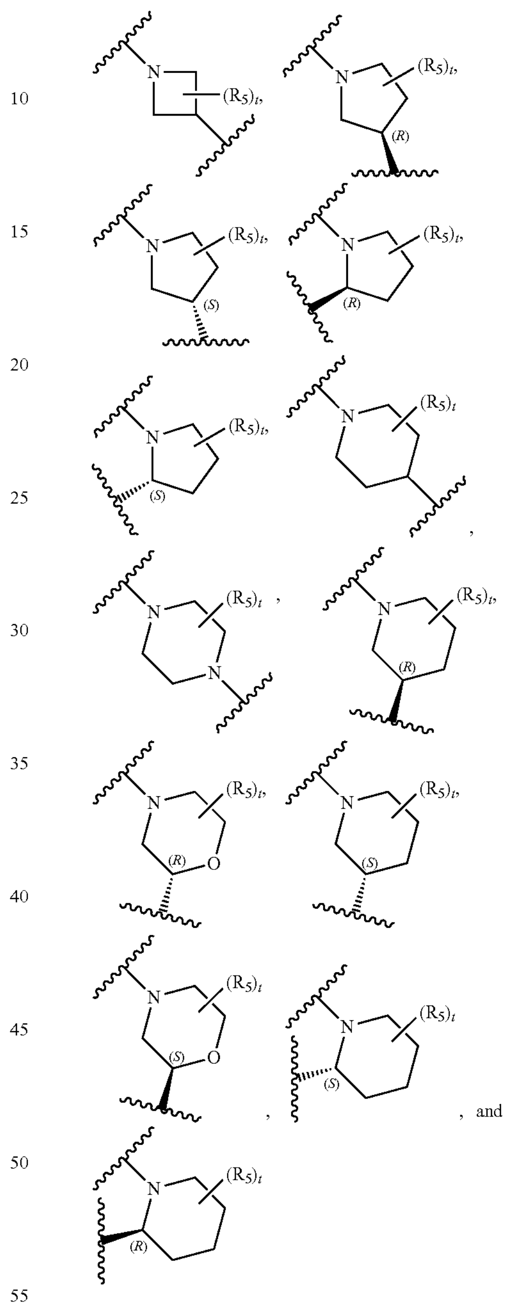

, , , , and with $R_5$ being $C_{1-3}$-alkyl, F, —$CH_2CN$ or —CN and t being 0, 1 or 2.

Furthermore, the invention relates to the synthesis of compounds of formula (I, II) as defined hereinbefore including tautomers, solvates, intermediates, prodrugs and salts of said compounds. A second aspect of the invention relates to the compound according to the first aspect of the invention for use in the treatment of a disease.

Another aspect of the invention relates to a compound according to the first aspect of the invention for use in the treatment of a disease, wherein the disease caused by an activating mutation of the PI3KCA gene or activation of a class I PI3K, in particular PI3Kα. The activation of the class I PI3K, in particular PI3Kα, can occur by cell surface receptors, upstream over-expressed or mutated up-stream activators or an activating mutation of the PI3KCA gene or PI3K-interacting and regulatory proteins, including the gene products of PIK3R1, PIK3R1, PIK3R1.

A third aspect of the invention relates to a compound according to the first aspect of the invention for use in the treatment of tumor disease, overgrowth syndrome, neurological disease, immunological disease.

In certain embodiments, the tumor is a solid tumor and/or the tumor disease is selected from lymphoma and leukemia.

In certain embodiments, the compound according to the first aspect of the invention is for use in the treatment of a proliferative disease; any benign or malignant tumor; a tumors emerging from sarcoma; lung; bronchus; prostate; breast; pancreas; gastrointestinal cancer; colon; rectum; colon carcinoma; colorectal adenoma; thyroid; liver; intrahepatic bile duct; hepatocellular; adrenal gland; stomach; gastric; glioma; glioblastoma; endometrial; melanoma; kidney; renal pelvis; urinary bladder; uterine corpus; uterine cervix; vagina; ovary; multiple myeloma; esophagus; the treatment of leukaemia; acute myelogenous leukemia; chronic myelogenous leukemia; lymphocytic leukemia; myeloid leukemia; brain; a carcinoma of the brain; oral cavity and pharynx; larynx; small intestine; non-Hodgkin lymphoma; melanoma; villous colon adenoma; a neoplasia; a neoplasia of epithelial character; lymphomas; the treatment of mammary carcinomas; basal cell carcinomas; squamous cell carcinomas; actinic keratosis; tumor diseases, including solid tumors; a tumor of the neck or head; polycythemia vera; essential thrombocythemia; myelofibrosis with myeloid metaplasia; and Waldenstrom's macroglobulinemia; Cowden's disease and multiple hamartoma syndrome including sporadic cancers such as breast, thyroid, uterine cancers, and other cancers emerging in patients with these syndromes; PIK3CA-related overgrowth spectrum (PROS)-related disorders, including Fibroadipose hyperplasia (also called fibroadipose overgrowth), CLOVES syndrome, Megalencephaly-capillary malformation syndrome (MCAP syndrome), Hemihyperplasia-multiple lipomatosis syndrome (HHML syndrome), Hemimegalencephaly, and Facial and infiltrating lipomatosis in other organs; general vascular and lymphatic malformations, and tumor neovascularization; ocular neovascularization and macular degeneration (AMD), proliferative and diabetic retinopathy (PDR), and retinopathy of prematurity (ROP)".

The invention also relates to such PI3K-targeting compounds as chemotherapeutic agents with anti-cancer activity, pharmaceutical formulations thereof, which are potentially useful in treatment of disease, conditions and/or disorders modulated by augmented cell division, growth, migration, adhesion and metastasis. The compounds may inhibit tumor growth in mammals, and may be useful for treating human cancer patients.

The invention also refers to the ability to tune the intrinsic reactivity of the inhibitors by modulating the exit vector of the warhead (meta, ortho position on 6-, 5-membered ring or on 4-membered ring).

Additionally, to cancer treatment, the present invention also relates to the treatment of pathogenic cellular states caused by cell over-activation using such compounds. Molecules targeting PI3K can be used to treat a variety of hyper-proliferative diseases for the treatment or prevention of a disease or condition modulated by PI3Ks.

The invention also relates to such PI3K-targeting compounds as chemical probes to dissect the role(s) of PI3K isoforms in cancer and metabolism.

In addition, the invention relates to methods of using such compounds for in vitro, in situ, and in vivo diagnostic procedures or treatment of mammalian cells, organisms, or associated pathological conditions, or production processes.

In further aspects, the invention relates to pharmaceutical compositions comprising a compound of formula (I, II) as defined hereinbefore, and to methods of preventing or treating a disease or disorder modulated by PI3Ks, in particular treating a hyperproliferative disorder.

Further aspects of the invention relate to the use of an effective amount of compounds of formula (I, II) as defined hereinbefore alone or in combination with standard treatment, such as chemotherapy, radiotherapy, targeted therapy or immunotherapy of a disease or disorder modulated by PI3Ks, in particular hyperproliferative disorders.

In further aspects, the invention relates to the use of compounds of formula (III) as linkers in the design and synthesis of covalent compounds targeting protein kinases.

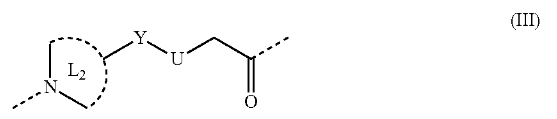

(III)

wherein

U is equal to NH, $NCH_3$, O or $CH_2$;

Y is equal to CO, O or $CH_2$;

$L_2$ is azetidine or pyrrolidine or piperidine wherein the arrows denote the bonds in formula (III):

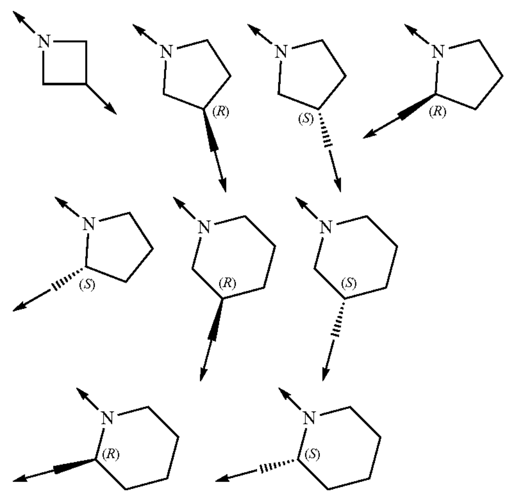

Another aspect of the invention includes methods of preparing, methods of separating, and methods of purifying compounds of formula (I, II, III), as defined hereinbefore including intermediates, prodrugs and salts of said compounds.

Another aspect of the invention includes novel intermediates useful for preparing compounds of formula (I, II, III) as defined hereinbefore.

Another aspect of the invention includes the novel, improved properties of compounds of formula (I, II, III) with respect to CNX-1351. These properties include, but are not limited to, in vitro and cellular potency, metabolic stability, solubility and drug-likeness properties.

Another aspect of the invention includes modulation of intrinsic reactivity of the inhibitors by modifying the exit vector (ortho or meta on 6- and 5-membered rings, or exit vector on 4-membered ring).

The cysteine residue of PI3Kα targeted for covalent modification by irreversible inhibitors of the present invention is the non-conserved Cys862.

Medical Treatment, Dosage Forms and Salts

Similarly, within the scope of the present invention is a method for treating tumor disease, overgrowth syndrome, neurological disease disorder and/or immunological disease disorder in a patient in need thereof, comprising administering to the patient a compound according to the above description.

Similarly, a dosage form for the prevention or treatment of tumor disease, overgrowth syndrome, neurological disease disorder and/or immunological disease disorder is provided, comprising compound according to any of the above aspects or embodiments of the invention.

The skilled person is aware that any specifically mentioned drug compound mentioned herein may be present as a pharmaceutically acceptable salt of said drug. Pharmaceutically acceptable salts comprise the ionized drug and an oppositely charged counterion. Non-limiting examples of pharmaceutically acceptable anionic salt forms include acetate, benzoate, besylate, bitatrate, bromide, carbonate, chloride, citrate, edetate, edisylate, embonate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate, phosphate, diphosphate, salicylate, disalicylate, stearate, succinate, sulfate, tartrate, tosylate, triethiodide and valerate. Non-limiting examples of pharmaceutically acceptable cationic salt forms include aluminium, benzathine, calcium, ethylene diamine, lysine, magnesium, meglumine, potassium, procaine, sodium, tromethamine and zinc.

Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

Topical administration is also within the scope of the advantageous uses of the invention. The skilled artisan is aware of a broad range of possible recipes for providing topical formulations, as exemplified by the content of Benson and Watkinson (Eds.), Topical and Transdermal Drug Delivery: Principles and Practice (1st Edition, Wiley 2011, ISBN-13: 978-0470450291); and Guy and Handcraft: Transdermal Drug Delivery Systems: Revised and Expanded ($2^{nd}$ Ed., CRC Press 2002, ISBN-13: 978-0824708610); Osborne and Amann (Eds.): Topical Drug Delivery Formulations ($1^{st}$ Ed. CRC Press 1989; ISBN-13: 978-0824781835).

Pharmaceutical Compositions and Administration

Another aspect of the invention relates to a pharmaceutical composition comprising a compound of the present invention, or a pharmaceutically acceptable salt thereof, and a pharmaceutically acceptable carrier. In further embodiments, the composition comprises at least two pharmaceutically acceptable carriers, such as those described herein.

In certain embodiments of the invention, the compound of the present invention is typically formulated into pharmaceutical dosage forms to provide an easily controllable dosage of the drug and to give the patient an elegant and easily handleable product.

In embodiments of the invention relating to topical uses of the compounds of the invention, the pharmaceutical composition is formulated in a way that is suitable for topical administration such as aqueous solutions, suspensions, ointments, creams, gels or sprayable formulations, e.g., for delivery by aerosol or the like, comprising the active ingredient together with one or more of solubilizers, stabilizers, tonicity enhancing agents, buffers and preservatives that are known to those skilled in the art.

The pharmaceutical composition can be formulated for enteral administration, particularly oral administration or rectal administration. In addition, the pharmaceutical compositions of the present invention can be made up in a solid form (including without limitation capsules, tablets, pills, granules, powders or suppositories), or in a liquid form (including without limitation solutions, suspensions or emulsions).

The pharmaceutical composition can be formulated for parenteral administration, for example by i.v. infusion, intradermal, subcutaneous or intramuscular administration.

The dosage regimen for the compounds of the present invention will vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. In certain embodiments, the compounds of the invention may be administered in a single daily dose, or the total daily dosage may be administered in divided doses of two, three, or four times daily.

In certain embodiments, the pharmaceutical composition of the present invention can be in unit dosage of about 1-1000 mg of active ingredient(s) for a subject of about 50-70 kg. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The pharmaceutical compositions of the present invention can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. They may be produced by standard processes, for instance by conventional mixing, granulating, dissolving or lyophilizing processes. Many such procedures and methods for preparing pharmaceutical compositions are known in the art, see for example L. Lachman et al. The Theory and Practice of Industrial Pharmacy, 4th Ed, 2013 (ISBN 8123922892).

Method of Manufacture and Method of Treatment According to the Invention

The invention further encompasses, as an additional aspect, the use of a compound according to the first aspect of the invention as identified herein, or its pharmaceutically acceptable salt, as specified in detail above, for use in a method of manufacture of a medicament for the treatment or prevention of a condition selected from tumor disease, overgrowth syndrome, neurological disease disorder and/or immunological disease disorder.

Similarly, the invention encompasses methods of treatment of a patient having been diagnosed with a disease associated with tumor disease, overgrowth syndrome, neurological disease disorder and/or immunological disease disorder. This method entails administering to the patient an effective amount of compound as identified herein (SPECIFY), or its pharmaceutically acceptable salt, as specified in detail herein.

Wherever alternatives for single separable features such as, for example, an isotype protein or coding sequence, ligand type or medical indication are laid out herein as "embodiments", it is to be understood that such alternatives may be combined freely to form discrete embodiments of the invention disclosed herein. Thus, any of the alternative embodiments for a detectable label may be combined with any of the alternative embodiments of ligand and these combinations may be combined with any medical indication or diagnostic method mentioned herein.

The invention is further illustrated by the following examples and figures, from which further embodiments and advantages can be drawn. These examples are meant to illustrate the invention but not to limit its scope.

In certain embodiments, the compound according to the first aspect of the invention selected from compounds 1 to 50 as shown in the following table.

In certain embodiments, the compound according to the first aspect of the invention selected from compounds 1 to 52 as shown in the following table.

Most preferred are the following compounds shown by formula:

(The names of the corresponding structures were produced using ChemBioDraw Ultra, version 16.0).

Compound 1:

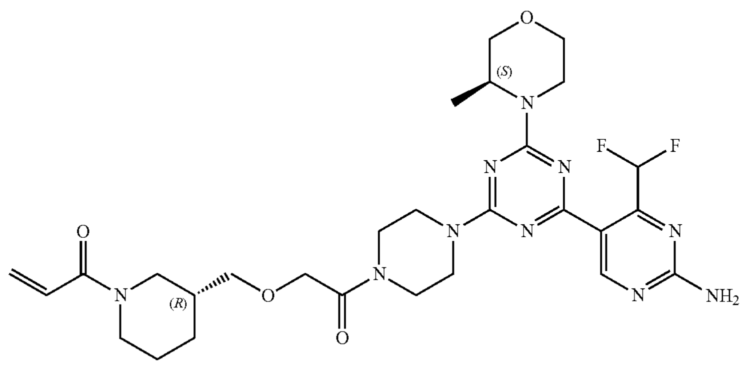

1-((R)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one Compound 2:

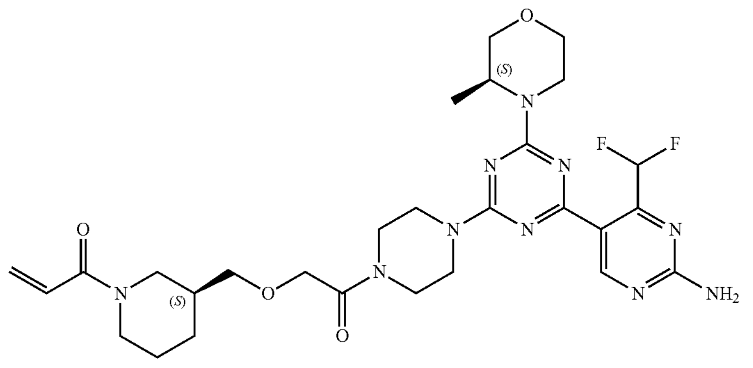

1-((S)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one Compound 3:

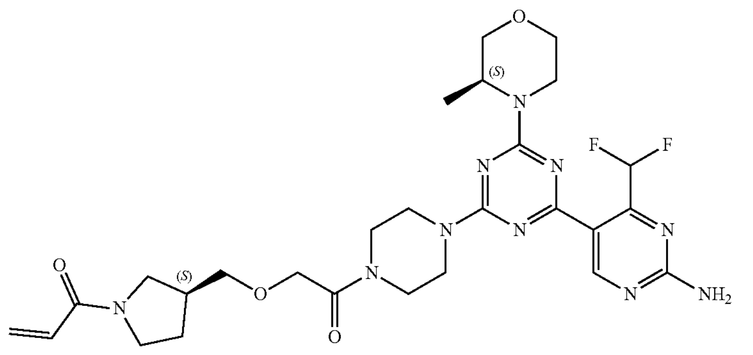

1-((S)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)pyrrolidin-1-yl)prop-2-en-1-one -continued Compound 4:

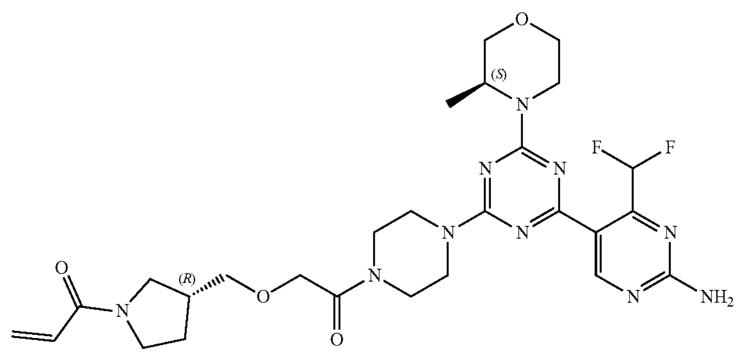

1-((R)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)pyrrolidin-1-yl)prop-2-en-1-one Compound 5:

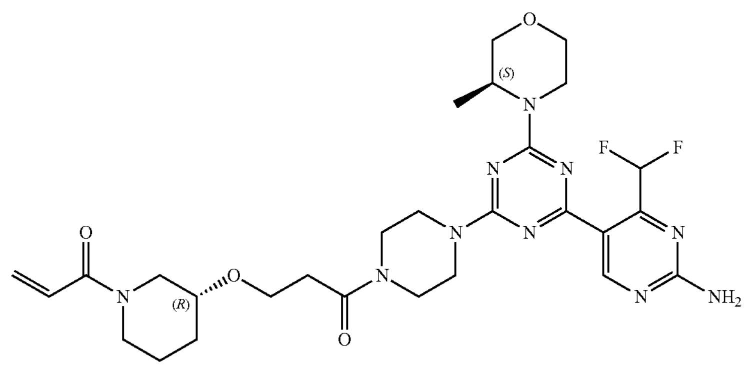

1-((R)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)piperidin-1-yl)prop-2-en-1-one Compound 6:

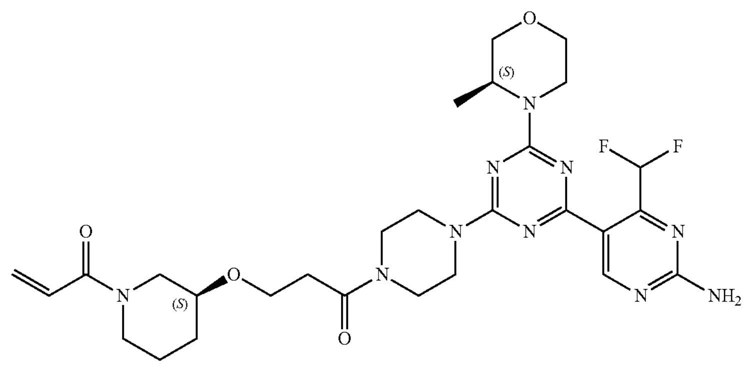

1-((S)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)piperidin-1-yl)prop-2-en-1-one Compound 7:

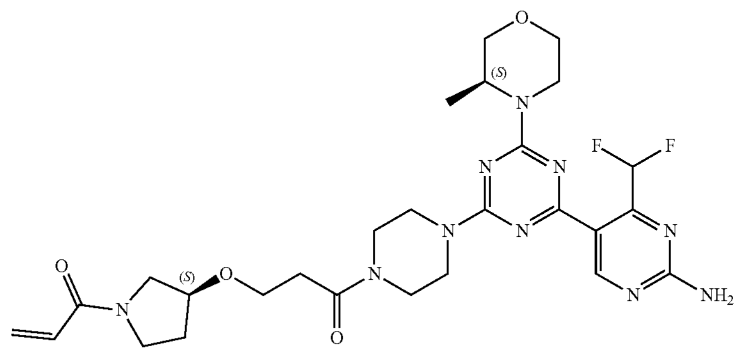

1-((S)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)pyrrolidin-1-yl)prop-2-en-1-one -continued Compound 8:

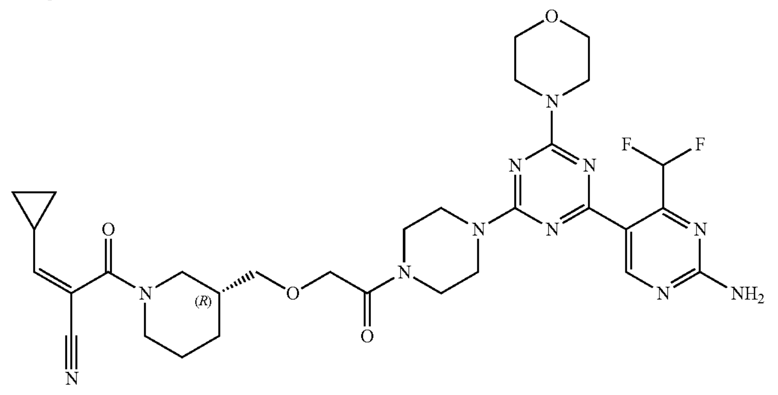

(R,Z)-2-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidine-1-carbonyl)-3-cyclopropylacrylonitrile Compound 9:

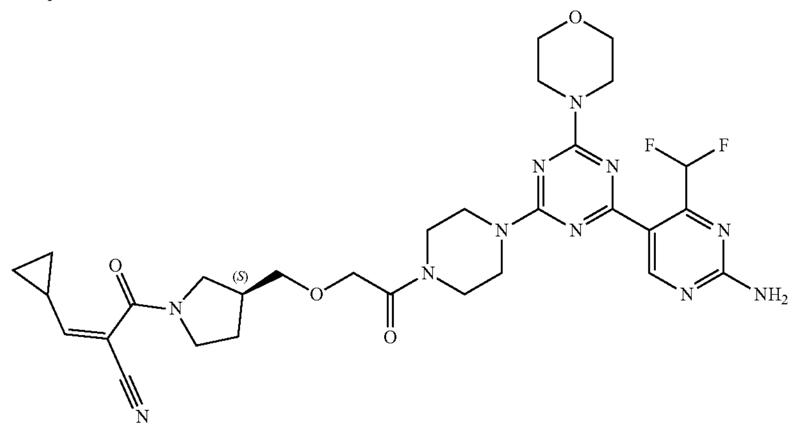

(S,Z)-2-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)pyrrolidine-1-carbonyl)-3-cyclopropylacrylonitrile Compound 10:

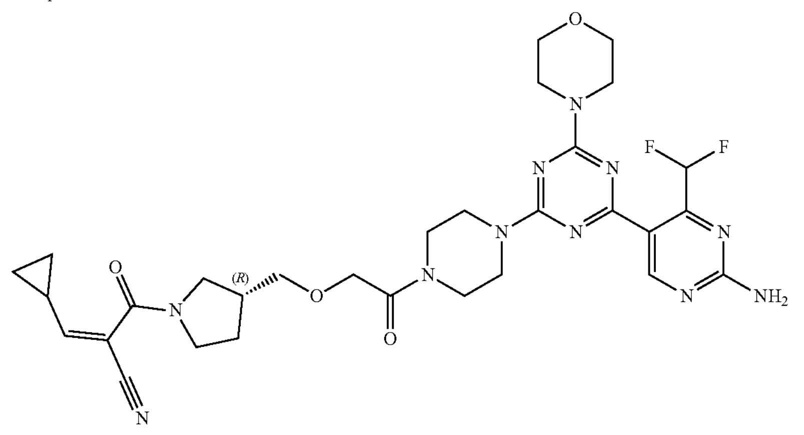

(R,Z)-2-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)pyrrolidine-1-carbonyl)-3-cyclopropylacrylonitrile -continued Compound 11:

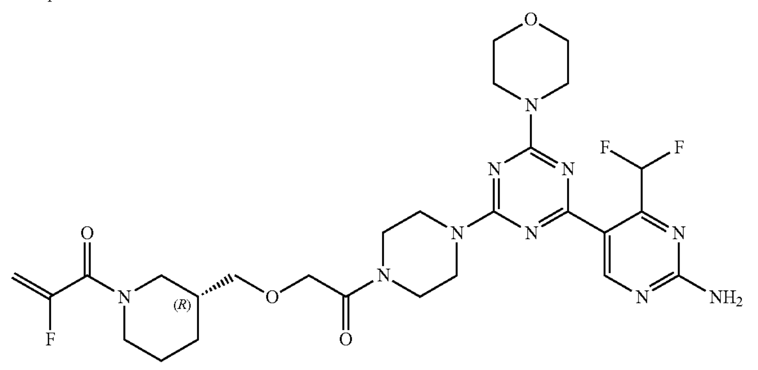

(R)-1-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-yl)-2-fluoroprop-2-en-1-one Compound 12:

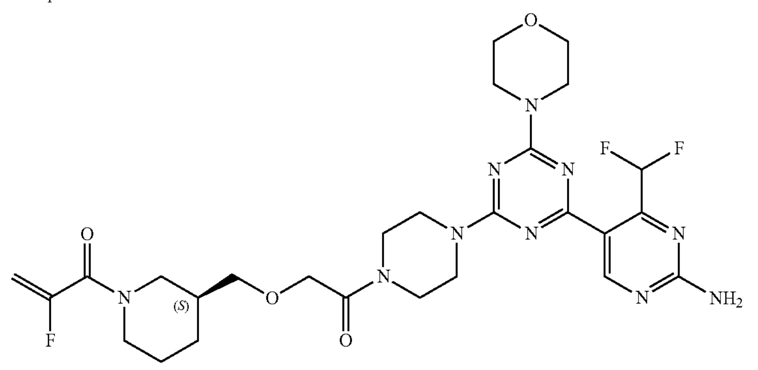

(S)-1-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-yl)-2-fluoroprop-2-en-1-one Compound 13:

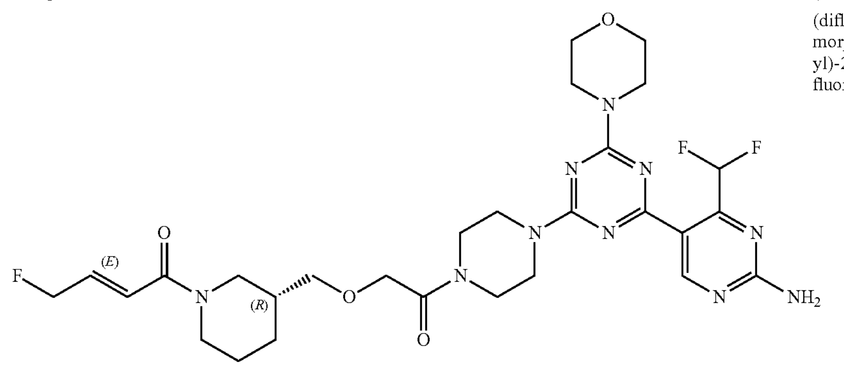

(R,E)-1-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-yl)-4-fluorobut-2-en-1-one Compound 14:

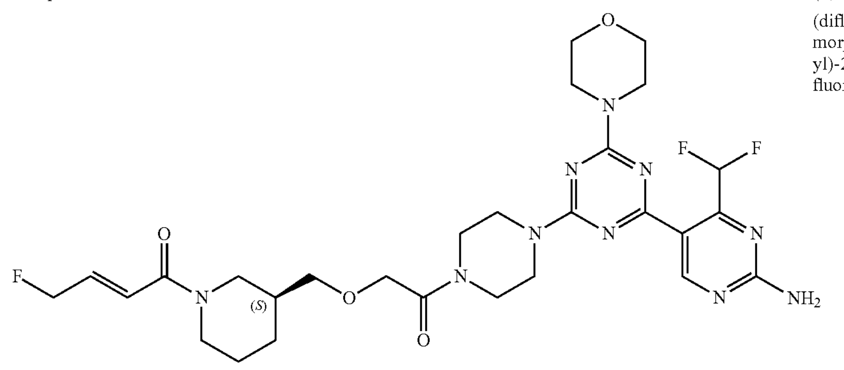

(S,E)-1-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-yl)-4-fluorobut-2-en-1-one -continued Compound 15:

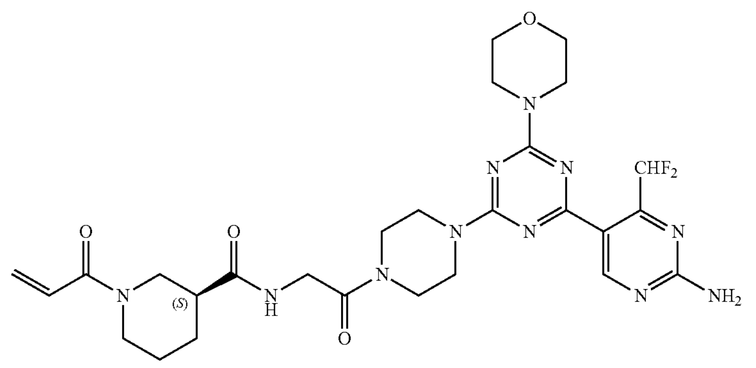

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)piperidine-3-carboxamide Compound 16:

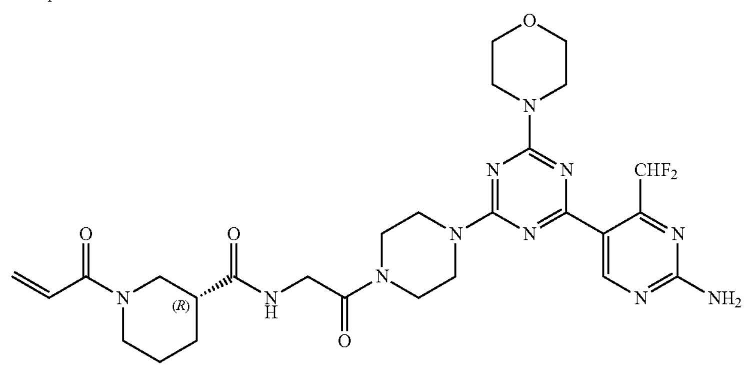

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)piperidine-3-carboxamide Compound 17:

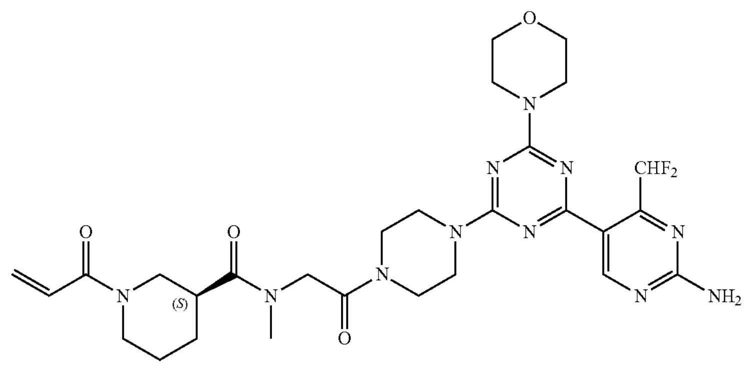

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-3-carboxamide Compound 18:

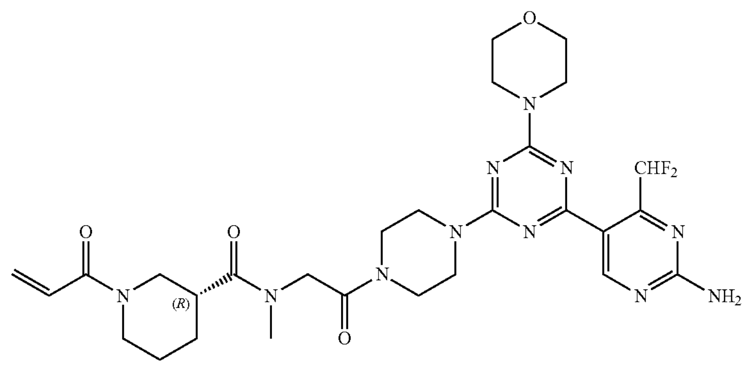

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-3-carboxamide -continued Compound 19:

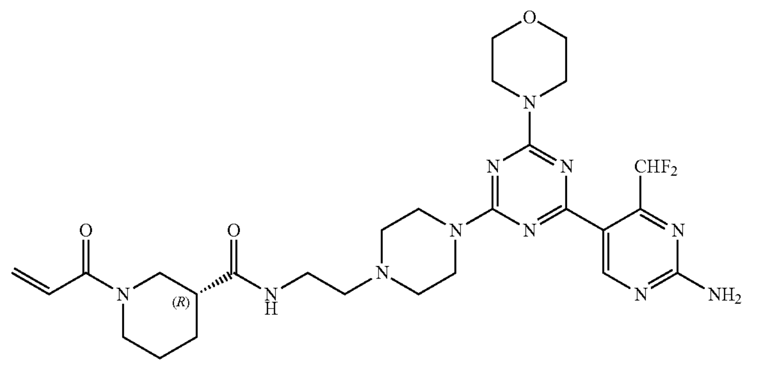

(R)-1-acryloyl-N-(2-(4-(4-(2-amino-4-(difluoromethyl)pyrimidin-5-yl)-6-morpholino-1,3,5-triazin-2-yl)piperazin-1-yl)ethyl)piperidine-3-carboxamide Compound 20:

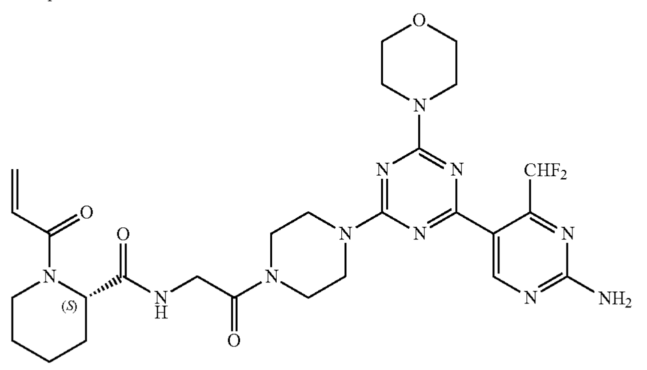

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)piperidine-2-carboxamide Compound 21:

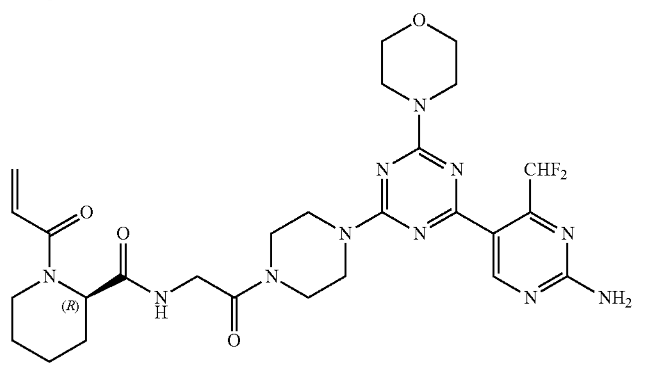

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)piperidine-2-carboxamide Compound 22:

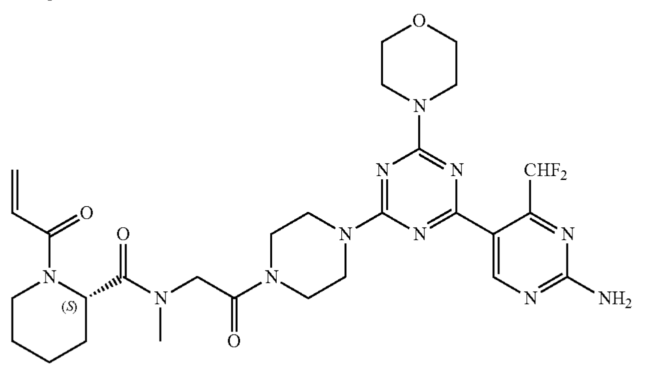

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-2-carboxamide -continued Compound 23:

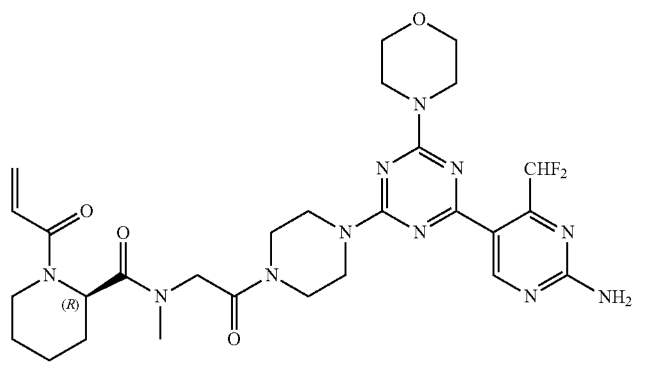

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-2-carboxamide Compound 24:

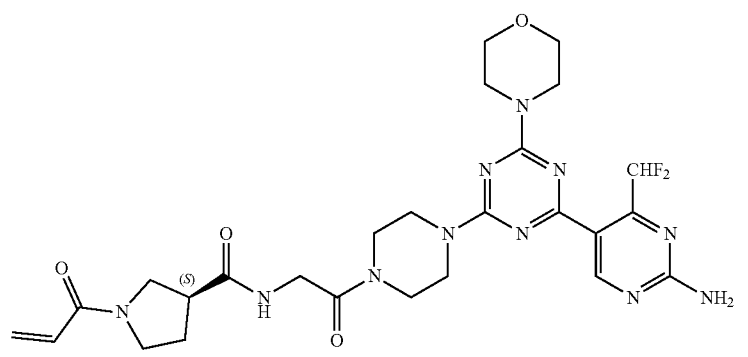

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-3-carboxamide Compound 25:

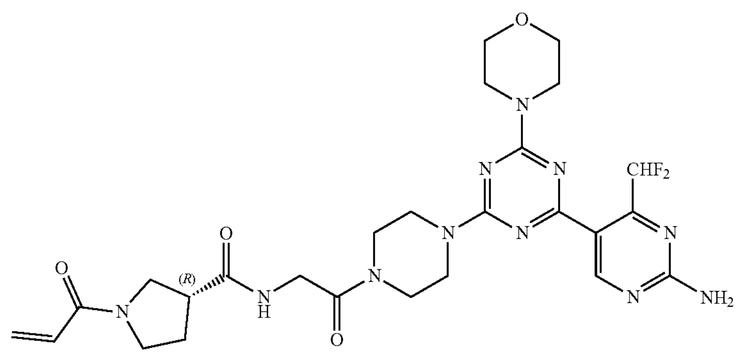

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-3-carboxamide Compound 26:

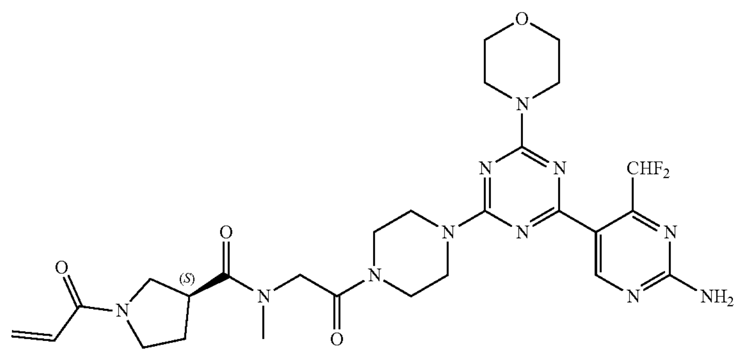

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpyrrolidine-3-carboxamide -continued Compound 27:

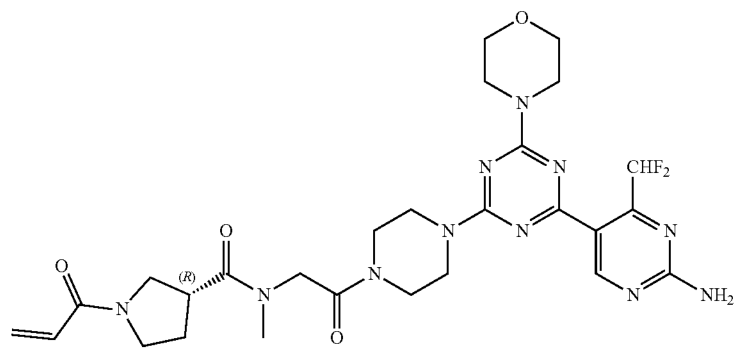

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpyrrolidine-3-carboxamide Compound 28:

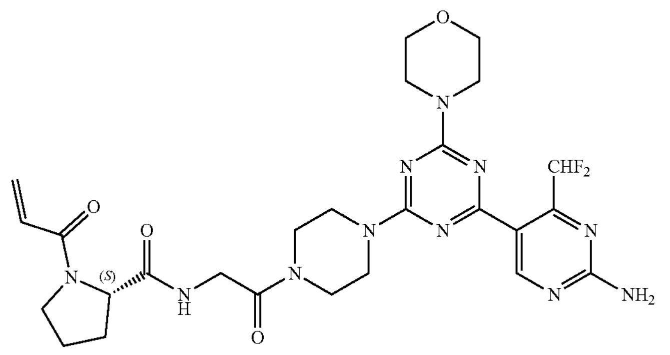

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-2-carboxamide Compound 29:

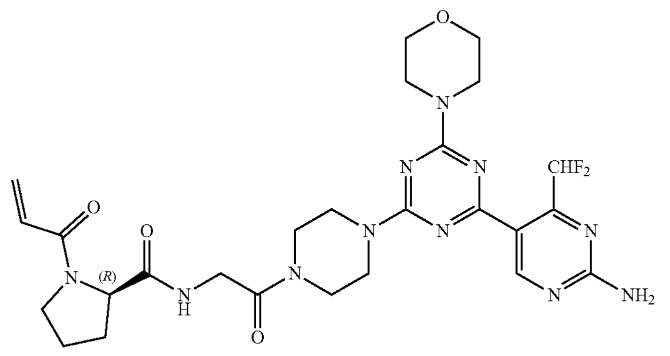

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-2-carboxamide Compound 30:

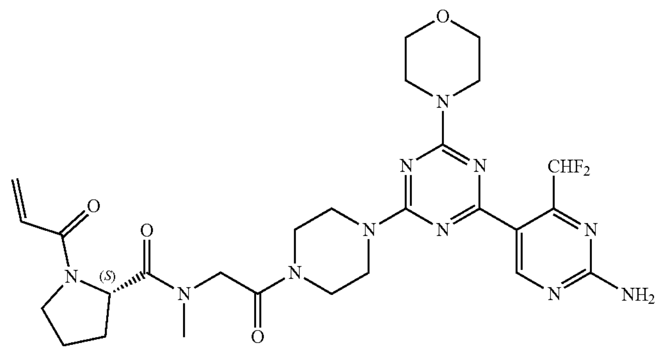

(S)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpyrrolidine-2-carboxamide -continued Compound 31:

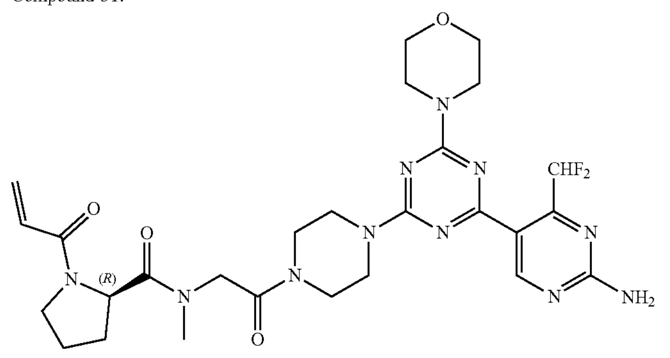

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpyrrolidine-2-carboxamide Compound 32:

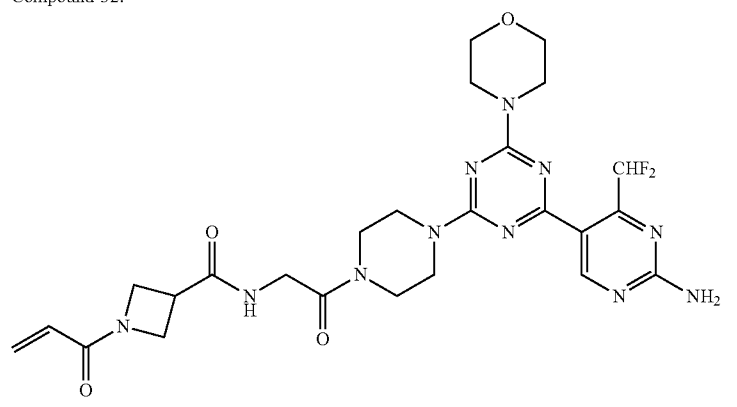

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)azetidine-3-carboxamide Compound 33:

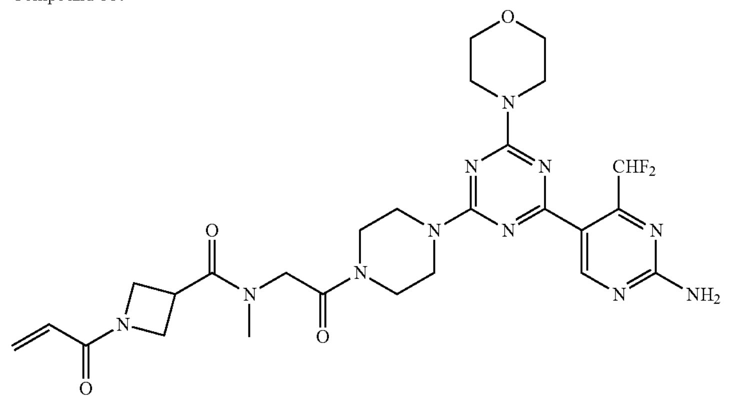

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylazetidine-3-carboxamide Compound 34:

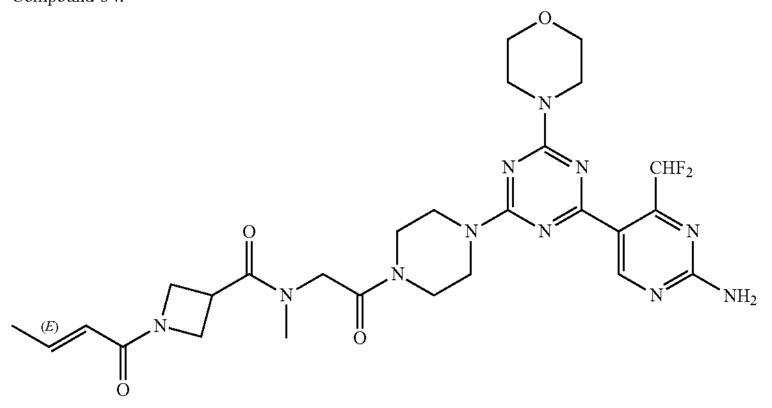

(E)-N-(2-(4-(4-(2-amino-4-(difluoromethyl)pyrimidin-5-yl)-6-morpholino-1,3,5-triazin-2-yl)piperazin-1-yl)-2-oxoethyl)-1-(but-2-enoyl)-N-methylazetidine-3-carboxamide -continued Compound 35:

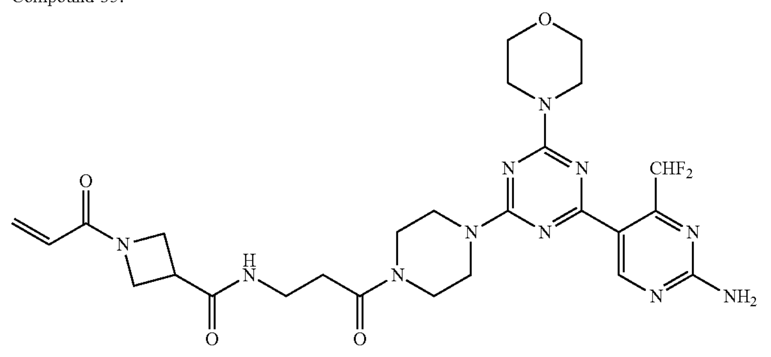

1-acryloyl-N-(3-(4-(4-(2-amino-4-(difluoromethyl)pyrimidin-5-yl)-6-morpholino-1,3,5-triazin-2-yl)piperazin-1-yl)-3-oxopropyl)azetidine-3-carboxamide Compound 36:

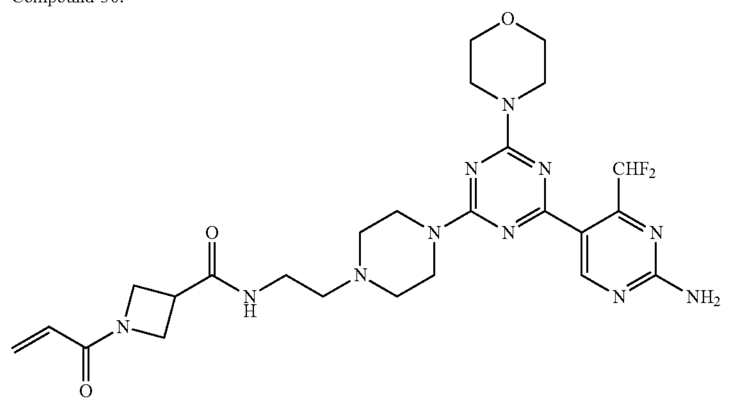

1-acryloyl-N-(2-(4-(4-(2-amino-4-(difluoromethyl)pyrimidin-5-yl)-6-morpholino-1,3,5-triazin-2-yl)piperazin-1-yl)ethyl)azetidine-3-carboxamide Compound 37:

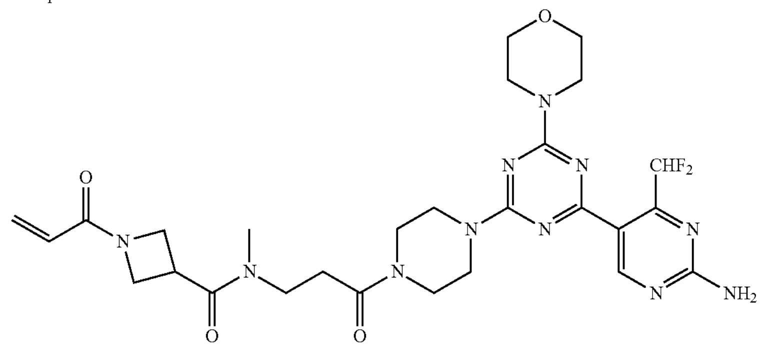

1-acryloyl-N-(3-(4-(4-(2-amino-4-(difluoromethyl)pyrimidin-5-yl)-6-morpholino-1,3,5-triazin-2-yl)piperazin-1-yl)-3-oxopropyl)-N-methylazetidine-3-carboxamide Compound 38:

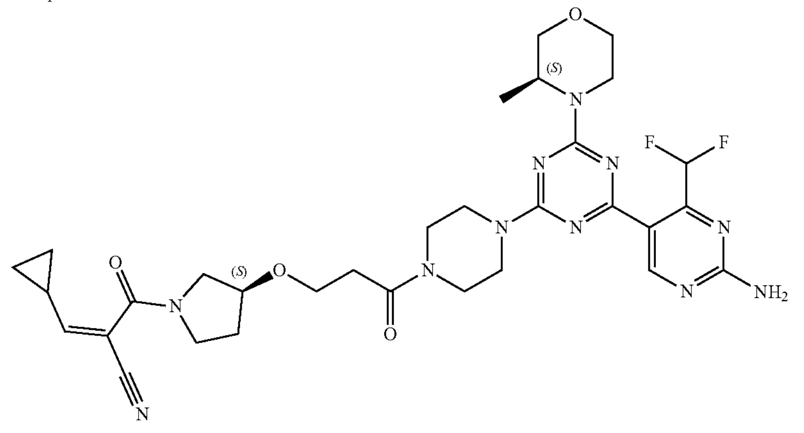

(Z)-2-((S)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)pyrrolidine-1-carbonyl)-3-cyclopropylacrylonitrile -continued Compound 39:

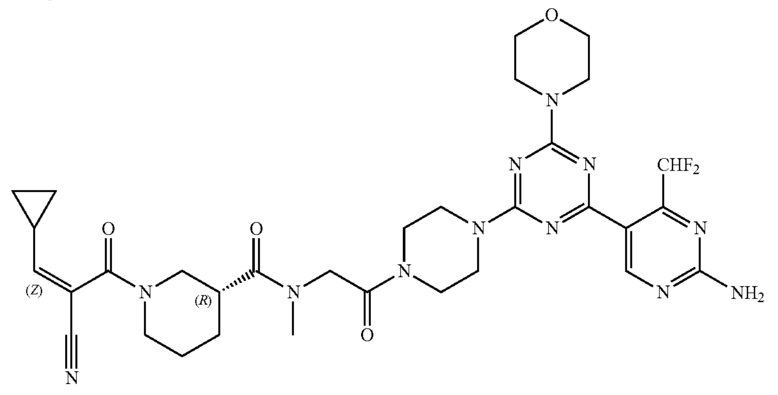

(R,Z)-N-(2-(4-(4-(2-amino-4-(difluoromethyl)pyrimidin-5-yl)-6-morpholino-1,3,5-triazin-2-yl)piperazin-1-yl)-2-oxoethyl)-1-(2-cyano-3-cyclopropylacryloyl)-N-methylpiperidine-3-carboxamide Compound 40:

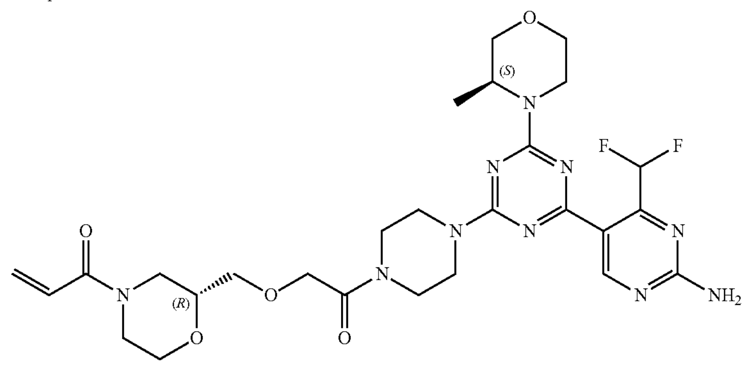

1-((R)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)morpholino)prop-2-en-1-one Compound 41:

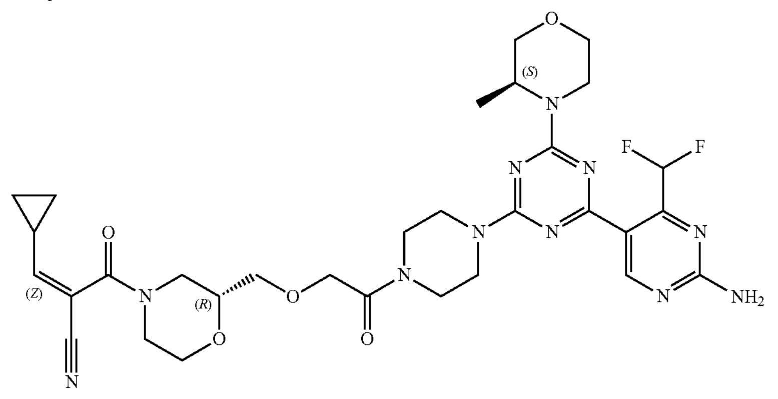

(Z)-2-((R)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)morpholine-4-carbonyl)-3-cyclopropylacrylonitrile Compound 42:

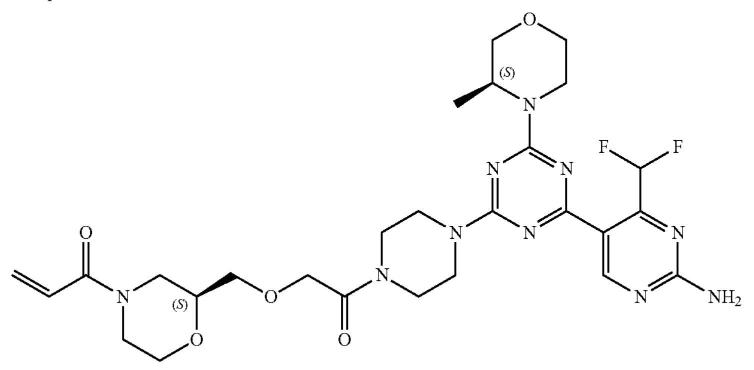

1-((S)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)morpholino)prop-2-en-1-one -continued Compound 43:

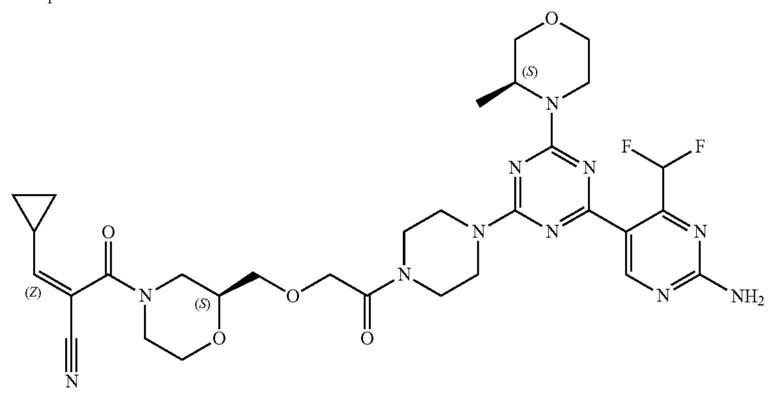

(Z)-2-((S)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)morpholine-4-carbonyl)-3-cyclopropylacrylonitrile Compound 44:

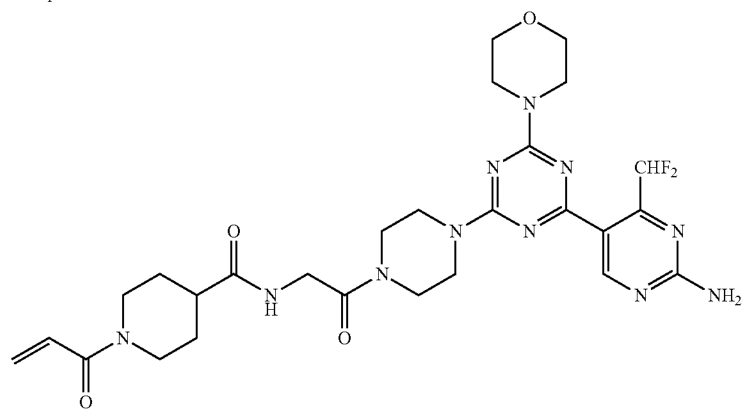

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)piperidine-4-carboxamide Compound 45:

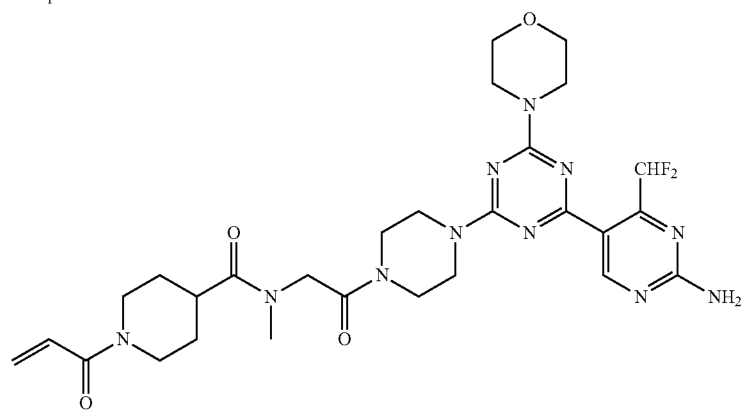

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-4-carboxamide -continued Compound 46:

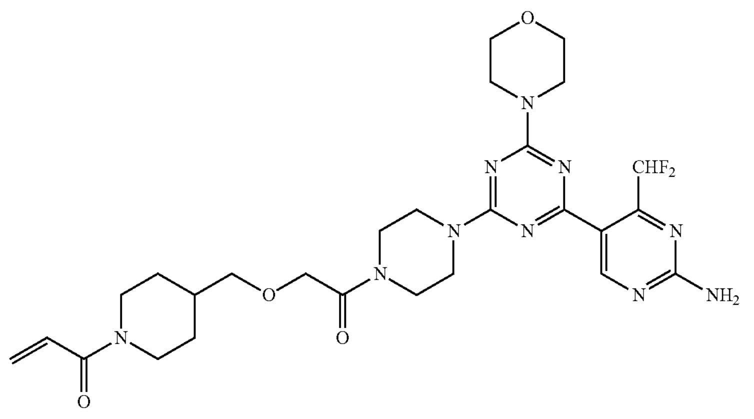 [SMILES: C=CC(=O)N1CCC(COCC(=O)N2CCN(c3nc(-c4cnc(N)nc4C(F)F)nc(N4CCOCC4)n3)CC2)CC1]

1-(4-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-yl)prop-2-en-1-one Compound 47:

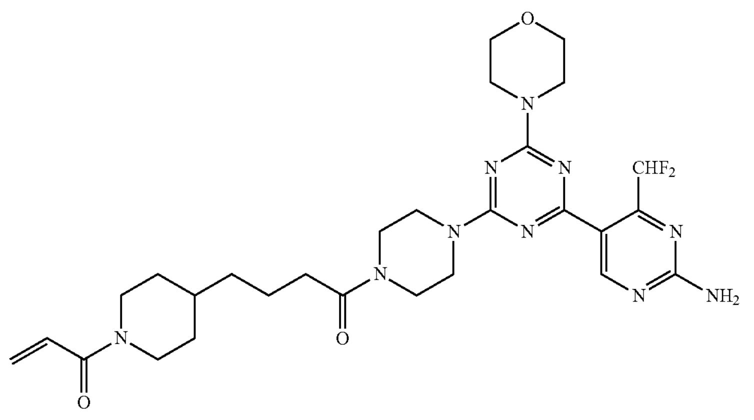 [SMILES: C=CC(=O)N1CCC(CCCC(=O)N2CCN(c3nc(-c4cnc(N)nc4C(F)F)nc(N4CCOCC4)n3)CC2)CC1]

4-(1-acryloylpiperidin-4-yl)-1-(4-(4-(2-amino-4-(difluoromethyl)pyrimidin-5-yl)-6-morpholino-1,3,5-triazin-2-yl)piperazin-1-yl)butan-1-one Compound 48:

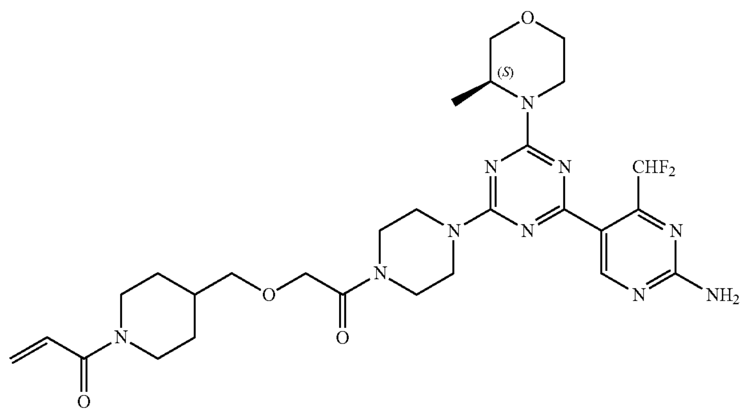

(S)-1-(4-((2-(4-(4-(2-amino-4-(difluoromethyl)pyrimidin-5-yl)-6-(3-methylmorpholino)-1,3,5-triazin-2-yl)piperazin-1-yl)-2-oxoethoxy)methyl)piperidin-1-yl)prop-2-en-1-one -continued Compound 49:

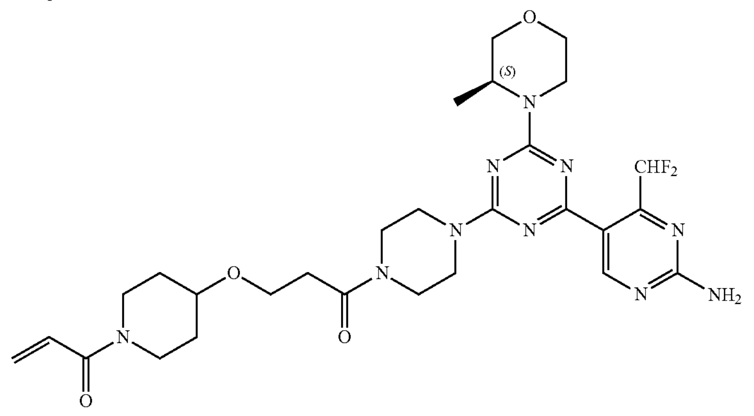

(S)-1-(4-(3-(4-(4-(2-amino-4-(difluoromethyl)pyrimidin-5-yl)-6-(3-methylmorpholino)-1,3,5-triazin-2-yl)piperazin-1-yl)-3-oxopropoxy)piperidin-1-yl)prop-2-en-1-one Compound 50:

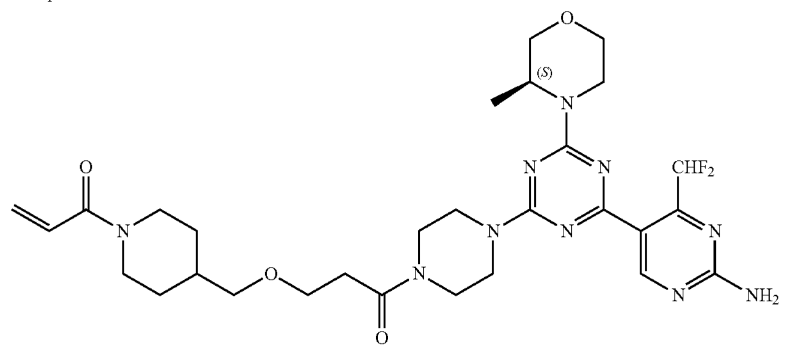

(S)-1-(4-((3-(4-(4-(2-amino-4-(difluoromethyl)pyrimidin-5-yl)-6-(3-methylmorpholino)-1,3,5-triazin-2-yl)piperazin-1-yl)-3-oxopropoxy)methyl)piperidin-1-yl)prop-2-en-1-one Compound 51:

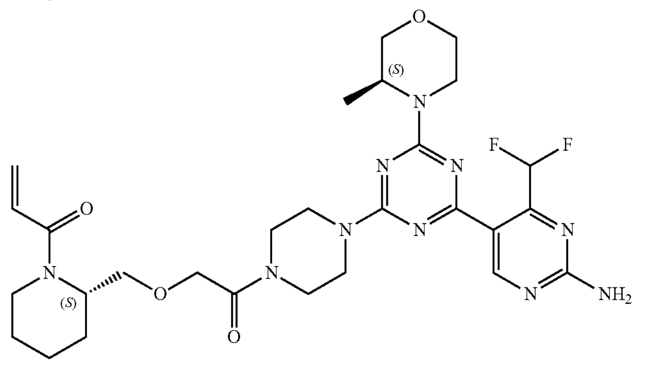

1-((S)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one Compound 52:

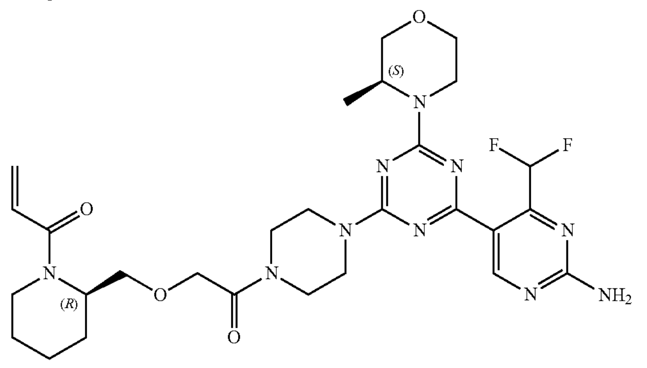

1-((R)-2-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one Most preferred linkers are the following compounds shown by formula (and their corresponding enantiomers):

Linker 1

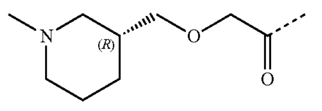

(R)-1-((1-methylpiperidin-3-yl)methoxy)propan-2-one

Linker 2

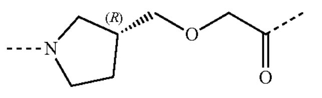

(R)-1-((1-methylpyrrolidin-3-yl)methoxy)propan-2-one

Linker 3

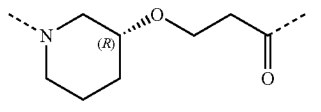

(R)-4-((1-methylpiperidin-3-yl)oxy)butan-2-one

Linker 4

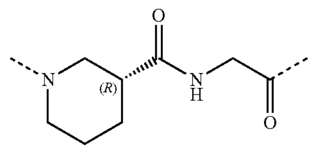

(R)-1-methyl-N-(2-oxopropyl)piperidine-3-carboxamide

Linker 5

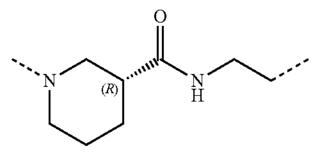

(R)-1-methyl-N-propylpiperidine-3-carboxamide

Linker 6

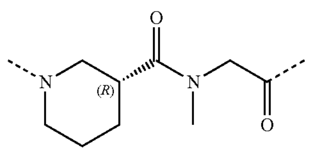

(R)-N,1-dimethyl-N-(2-oxopropyl)piperidine-3-carboxamide

Linker 7

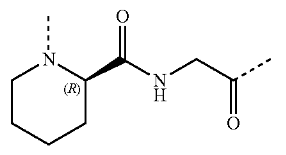

(R)-1-methyl-N-(2-oxopropyl)piperidine-2-carboxamide

Linker 8

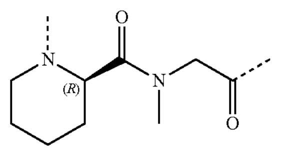

(R)-N,1-dimethyl-N-(2-oxopropyl)piperidine-2-carboxamide

-continued

Linker 9

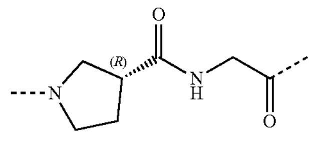

(R)-1-methyl-N-(2-oxopropyl)pyrrolidine-3-carboxamide

Linker 10

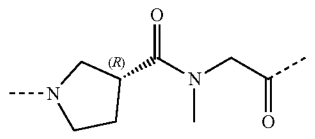

(R)-N,1-dimethyl-N-(2-oxopropyl)pyrrolidine-3-carboxamide

Linker 11

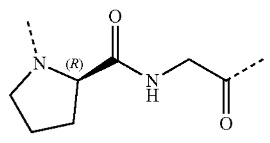

(R)-1-methyl-N-(2-oxopropyl)pyrrolidine-2-carboxamide

Linker 12

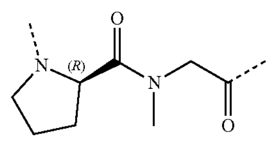

(R)-N,1-dimethyl-N-(2-oxopropyl)pyrrolidine-2-carboxamide

Linker 13

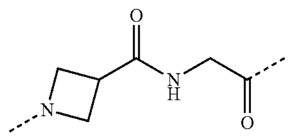

1-methyl-N-(2-oxopropyl)azetidine-3-carboxamide

Linker 14

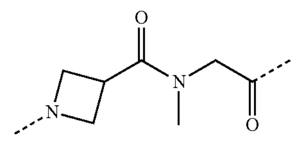

N,1-dimethyl-N-(2-oxopropyl)azetidine-3-carboxamide

BRIEF DESCRIPTION OF THE DRAWINGS

Summary data for some compounds of the invention in comparison to CNX-1351: intrinsic reactivity and in vitro data (Table 1); cellular potency (Table 2) for some of the compounds of the invention and CNX-1351.

FIG. 1. Metabolic stability of 18, 25 and 33 and CNX-1351 using rat liver microsomes fortified with Phase I metabolism cofactor NADPH.

EXAMPLES

Preparation of Compounds of the Invention

The compounds of the invention may be synthesized by synthetic routes that include processes analogous to those well known in the chemical arts, particularly in light of the description contained herein. The starting materials are generally available from commercial sources or are readily prepared using methods well known to those skilled in the art.

For illustrative purposes, Schemes 1-4 show general methods for preparing the compounds of the present invention as well as key intermediates. For a more detailed description of the individual reaction steps, see the Examples herein below. Those skilled in the art will appreciate that other synthetic routes may be used to synthesize the compounds of the invention. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of the invention, protection and deprotection of remote functionality (e.g., primary or secondary amine) of intermediates may be necessary. The need for such protection will vary depending on the nature of the remote functionality and the conditions of the preparation methods. Suitable amino-protecting groups include tert-butyloxycarbonyl (BOC) or N,N-dimethylformamidinyl. The need for such protection is readily determined by one skilled in the art. For a general description of protecting groups and their use, see T. W. Greene, *Protective Groups in Organic Synthesis*, John Wiley & Sons, New York, 1991.

Scheme 1

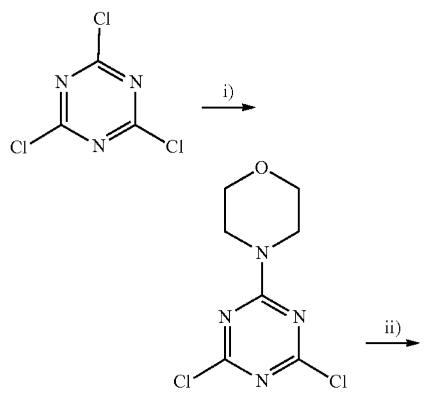

-continued

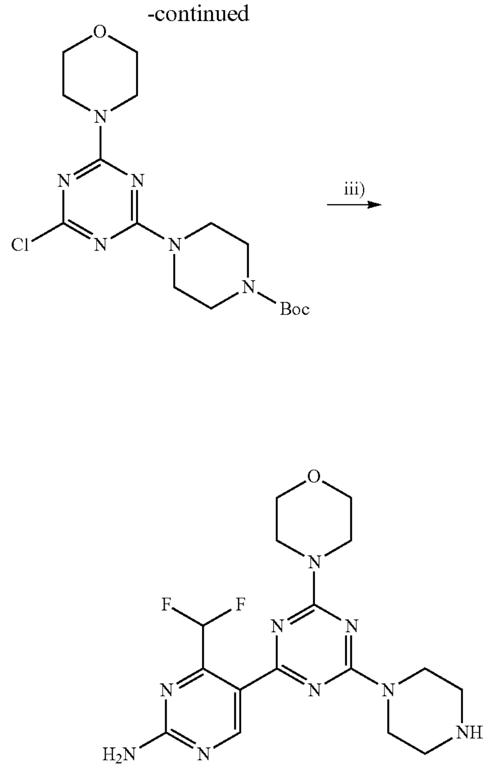

Scheme 1 shows a general method for the preparation of the inhibitors building block using nucleophilic aromatic substitutions and Suzuki coupling. Reagents and conditions: (i) $Et_3N$, DCM, −50° C., 3 h; (ii) 1-boc-piperazine, DIPEA, EtOH, 0° C.→r.t., 5 h; (iii) tert-Butyl N-[5-bromo-4-(difluoromethyl)pyrimidin-2-yl]-N-[(tert-butoxy)carbonyl]carbamate, bis(pinacolato)diboron, AcOK, $Pd(dppf)Cl_2$, dioxane, 95° C., 1.5 h, (2) monochloro-triazine, $XPhosPdG_2$ (cat.), $K_3PO_4$, $H_2O$, 100° C., o/n, (3) HCl, dioxane/$H_2O$, 80° C., o/n.

Scheme 2
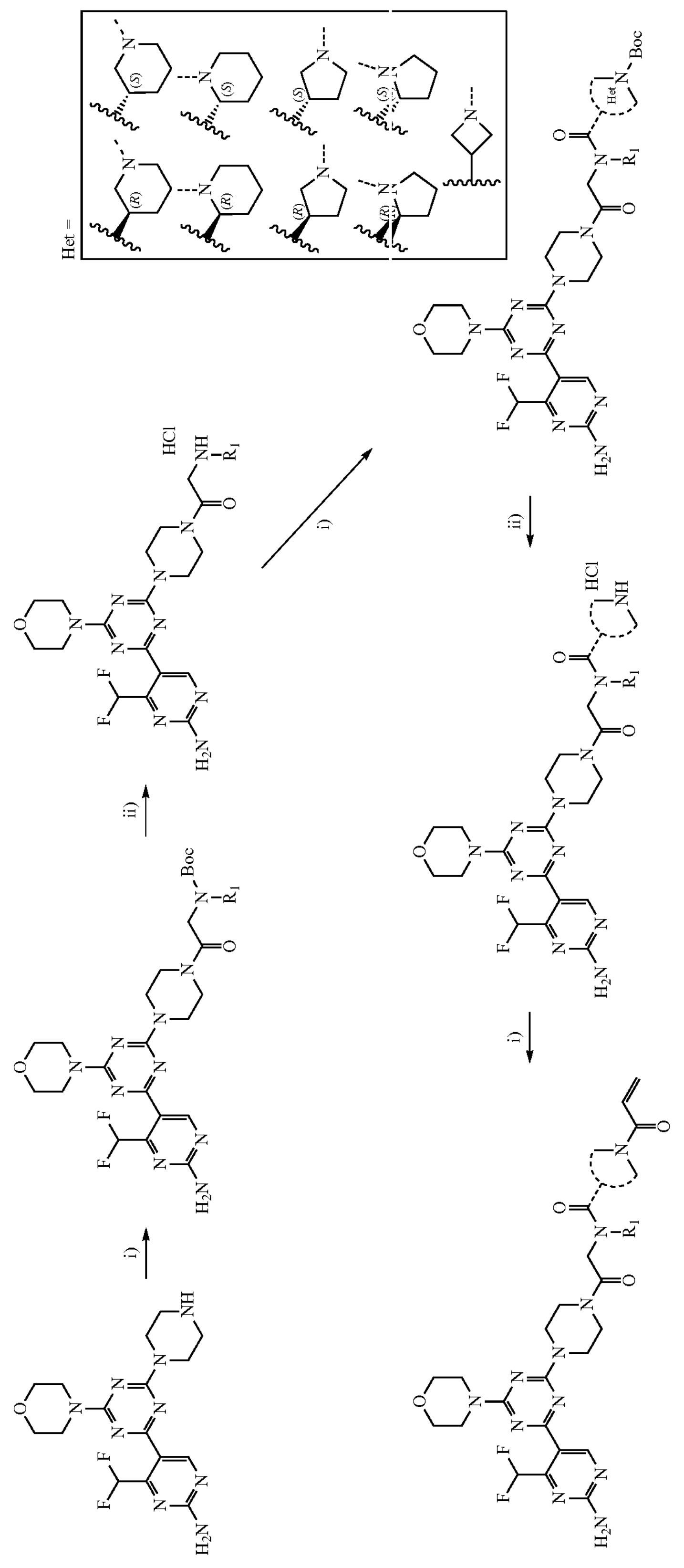

Scheme 2 shows a general method for the preparation of covalent inhibitors of formula (I) having an amide spacer. $R_1$ is H or $CH_3$. Reagents and conditions: (i) building block or HCl salt, HCTU, DIPEA, DMF, 0° C.→r.t., 4-16 h; (ii) HCl in dioxane (4 M), THF, r.t., 3-16 h.

Scheme 3
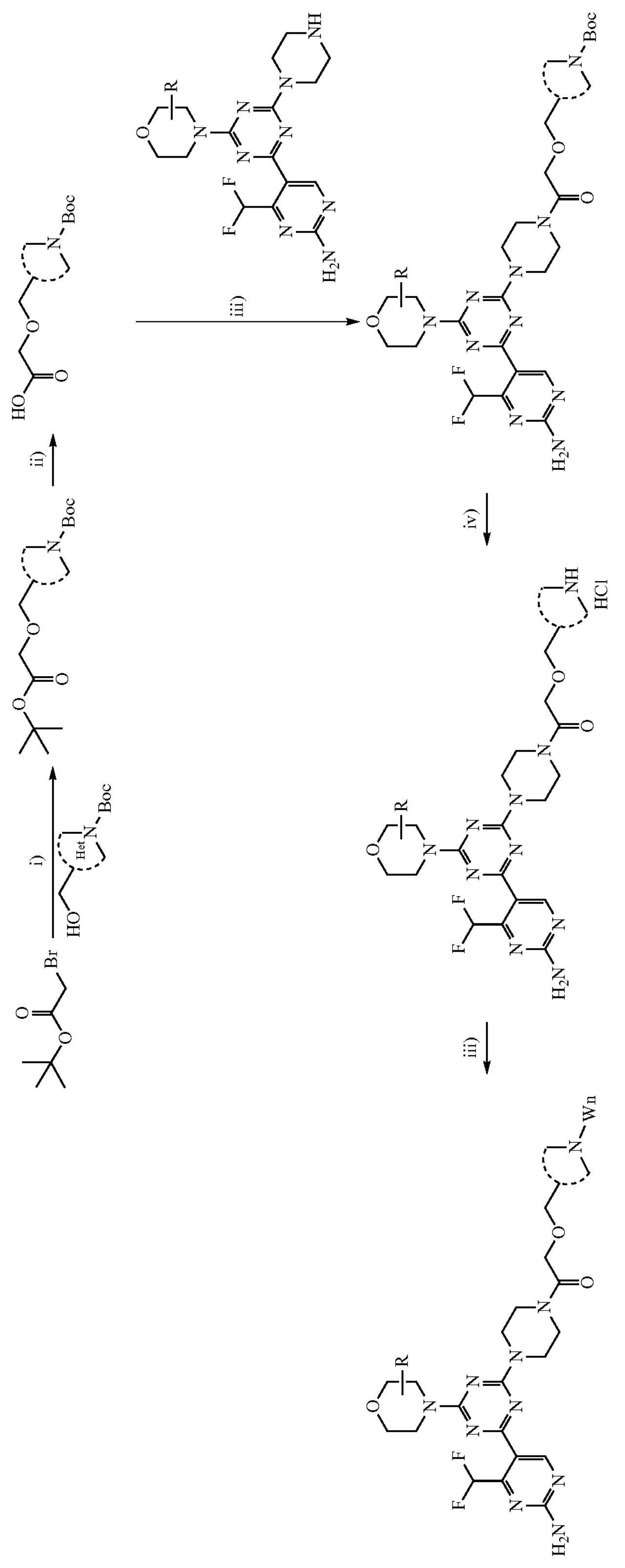
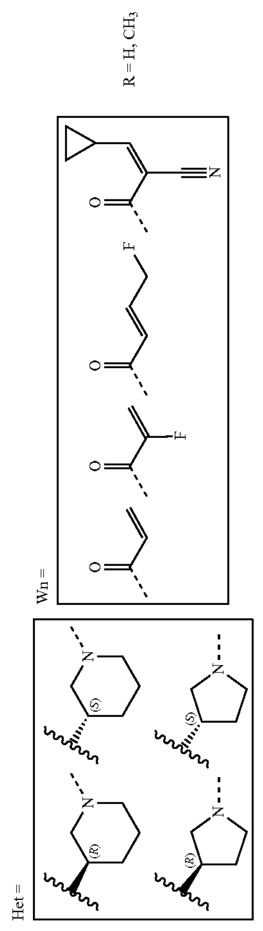

Scheme 3 shows the method for the preparation of compounds of formula (II). First the acid bearing an ether in the linker is synthesized by a nucleophilic substitution followed by a hydrolysis of the ester using a strong base in water/THF. Reagents and conditions: (i) NaH (60% dispersion in mineral oil), DMF, 0° C., 15 min; (ii) LiOH (5M in $H_2O$), THF; (iii) building block or HCl salt, HCTU, DIPEA, DMF, 0° C.→r.t., 2 h; (iv) HCl in dioxane (4 M), THF, r.t., o/n.

Scheme 4
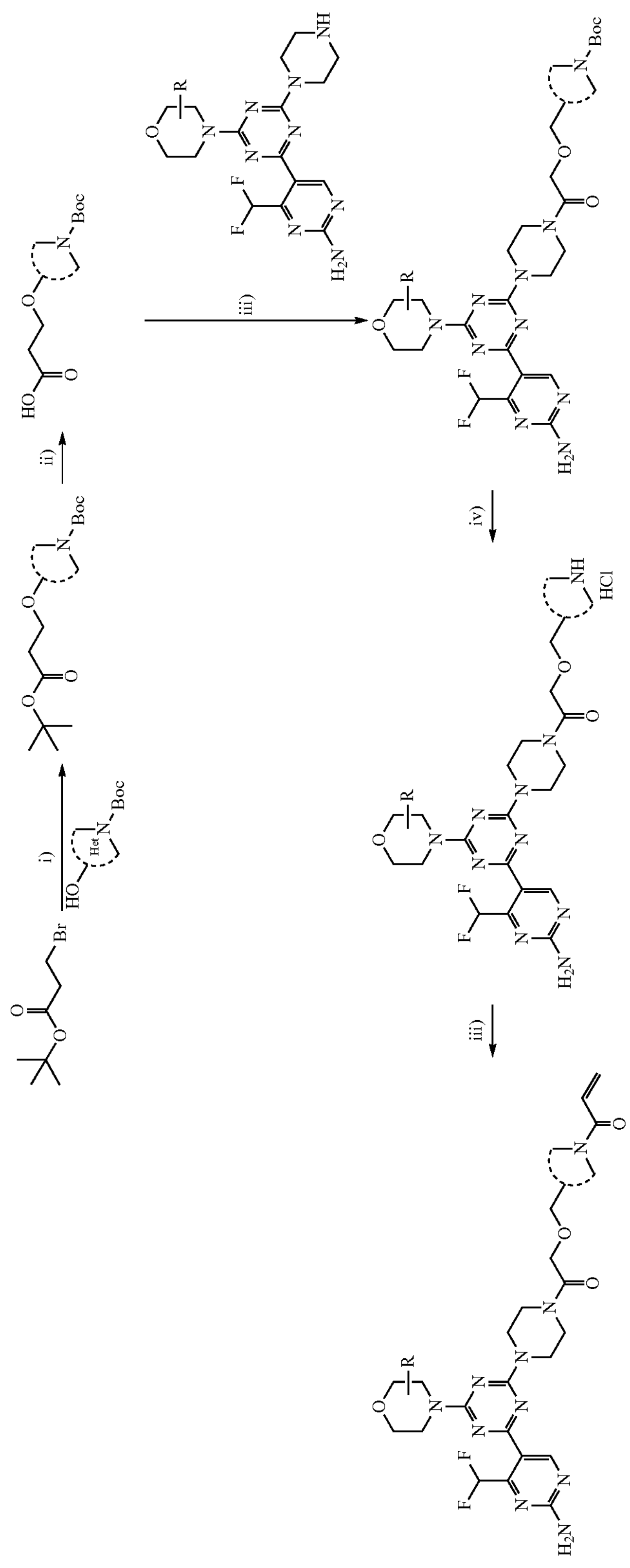
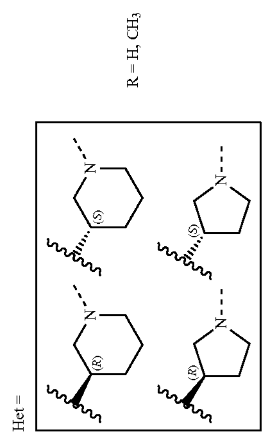

Scheme 4 shows the method for the preparation of compounds of formula (II). First the acid bearing an ether in the linker is synthesized by a nucleophilic substitution followed by a hydrolysis of the ester using a strong base in water/THF. Reagents and conditions: (i) NaH (60% dispersion in mineral oil), DMF, 0° C., 15 min; (ii) LiOH (5M in $H_2O$), THF; (iii) building block or HCl salt, HCTU, DIPEA, DMF, 0° C.→r.t., 2 h; (iv) HCl in dioxane (4 M), THF, r.t., o/n.

Methods of Separation

In the methods of preparing the compounds of this invention, it may be advantageous to separate reaction products from one another and/or from starting materials. The desired products of each step or series of steps are separated and/or purified to the desired degree of homogeneity by the techniques common in the art. Typically such separations involve extraction, crystallization from a solvent or solvent mixture, or chromatography. Chromatography can involve any number of methods including, for example: reverse-phase and normal phase; high, medium and low-pressure liquid chromatography methods and apparatus; small scale analytical; and preparative thin or thick layer chromatography, as well as techniques of small-scale thin layer and flash chromatography.

Selection of appropriate methods of separation depends on the nature of the materials involved, for example, presence or absence of polar functional groups in chromatography, stability of materials in acidic and basic media in multiphase extraction. One skilled in the art will apply techniques most likely to achieve the desired separation.

EXAMPLES

The Examples are intended to illustrate the present invention without restricting it.

The chemical reactions described in the Examples may be readily adapted to prepare a number of other inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

Reagents were purchased at the highest commercial quality from Acros Organics, Sigma-Aldrich, Apollo Scientific or Fluorochem and used without further purification. Solvents were purchased from Acros Organics in AcroSeal® bottles over molecular sieves. Grignard reactions, cross-coupling reactions and peptide-coupling reactions were carried out under nitrogen atmosphere in anhydrous solvents, and glassware was oven dried prior to use. Thin layer chromatography (TLC) plates were purchased from Merck KGAA (Polygram SIL/UV254, 0.2 mm silica with fluorescence indicator) and UV light (254 nm) was used to visualize the compounds. Flash chromatography was performed with Isco CombiFlash Companion systems using prepacked silica gel columns (40-60 μm particle size RediSep). $^{1}H$, $^{19}F$ and $^{13}C$ NMR spectra were recorded on a Bruker Avance 400 spectrometer. NMR spectra were obtained in deuterated solvents, namely $CDCl_3$ or $(CD_3)_2SO$. The chemical shift (δ values) are reported in ppm and corrected to the signal of the deuterated solvents (7.26 ppm ($^{1}H$ NMR) and 77.16 ppm ($^{13}C$ NMR) for $CDCl_3$; and 2.50 ppm ($^{1}H$ NMR) and 39.52 ppm ($^{13}C$ NMR) for $(CD_3)_2SO$. $^{19}F$ NMR spectra are calibrated relative to $CFCl_3$ (δ=0 ppm) as external standard. When peak multiplicities are reported, the following abbreviations are used: s (singlet), d (doublet), dd (doublet of doublets), t (triplet), td (triplet of doublets), q (quartet), doublet of quartets (dq), m (multiplet), br (broadened signal). Coupling constants, when given, are reported in Hertz (Hz). High resolution mass spectra (HRMS) were recorded on a Thermo Fisher Scientific LTQ Orbitrap XL (nanoESI-MS) spectrometer. MALDI-ToF mass spectra were obtained on a Voyager-De™ Pro measured in m/z. The chromatographic purity of final compounds was determined by high performance liquid chromatography (HPLC) analyses on an Ultimate 3000SD System from ThermoFisher with LPG-3400SD pump system, ACC-3000 autosampler and column oven, and DAD-3000 diode array detector. An Acclaim-120 C18 reversed-phase column from ThermoFisher was used as stationary phase. Gradient elution (5:95 for 0.2 min, 5:95→100:0 over 10 min, 100:0 for 3 min) of the mobile phase consisting of $CH_3CN/MeOH:H_2O_{(10.90)}$ was used at a flow rate of 0.5 mL/min at 40° C. The purity of all final compounds was higher than 95%.

The following abbreviations are used hereinafter: DMSO (dimethyl sulfoxide), HCl (hydrochloric acid), M (molar), MALDI (Matrix-assisted Laser Desorption/Ionization), HRMS (High resolution mass spectra), MS (mass spectrometry), PBS (phosphate buffered saline), TLC (thin layer chromatography).

Preparation of Intermediate Compounds

The following methods were used to prepare the intermediates compounds used to produce compounds of formula (I, II).

Method 1: tert-butyl 4-(4-chloro-6-morpholino-1,3,5-triazin-2-yl)piperazine-1-carboxylate

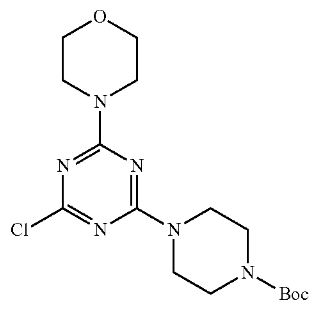 [SMILES: CC(C)(C)OC(=O)N1CCN(c2nc(Cl)nc(N3CCOCC3)n2)CC1]

To a solution of 2,4-dichloro-6-(morpholin-4-yl)-1,3,5-triazine (20.7 g, 87.9 mmol, 0.9 equiv) in ethanol, DIPEA (16.2 g, 21.4 ml, 125.6 mmol, 1.3 equiv) and 1-Boc-piperazine (18.0 g, 96.6 mmol, 1.0 equiv) were added at 0° C. The reaction mixture was stirred at room temperature for 5 hours. The solvent was removed under reduced pressure. Dichloromethane (300 mL) was added and the resulting organic layer was washed with an aqueous saturated $NaHSO_4$-solution (4×200 mL). The organic layer was dried over anhydrous $Na_2SO_4$, filtered and concentrated under reduced pressure. The product was recrystallized from dichloromethane/heptanes to obtain tert-butyl 4-(4-chloro-6-morpholino-1,3,5-triazin-2-yl)piperazine-1-carboxylate as a colorless solid (22.7 g, 58.9 mmol, 80%). MALDI-MS: m/z=385.643 $[M+H]^+$. HPLC: $t_R$=6.53 min (100.0% purity).

Method 2: 4-(difluoromethyl)-5-(4-morpholino-6-(piperazin-1-yl)-1,3,5-triazin-2-yl)pyrimidin-2-amine

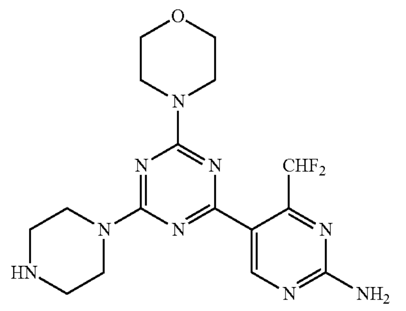 [SMILES: Nc1ncc(-c2nc(N3CCNCC3)nc(N3CCOCC3)n2)c(C(F)F)n1]

Step 1. tert-Butyl N-[5-bromo-4-(difluoromethyl)pyrimidin-2-yl]-N-[(tert-butoxy)carbonyl]carbamate (7.00 g, 16.50 mmol, 1.0 equiv), Bis(pinacolato)diboron (6.29 g, 24.75 mmol, 1.5 equiv), potassium acetate (5.02 g, 51.15 mmol, 3.1 equiv), [1,1'-bis(diphenylphosphino)ferrocene] dichloropalladium(II) (Pd(dppf)$Cl_2$, 1.21 g, 1.65 mmol, 0.1 equiv) were charged in flask under nitrogen atmosphere. Absolute 1,4-dioxane (40 mL) was added and the mixture was stirred at 95° C. for 1.5 hour. After completion of the reaction, the mixture was allowed to cool down to room temperature. Step 2. Monochloro-triazine 4-(4-chloro-6-morpholino-1,3,5-triazin-2-yl)piperazine-1-carboxylate (6.99 g, 18.15 mmol, 1.1 equiv), chloro(2-dicyclohexylphosphino-2',4',6'-triisopropyl-1,1'-biphenyl)[2-(2'-amino-1,1'-biphenyl)]palladium(II) (XPhos Pd G2, 0.519 g, 0.66 mmol, 0.04 equiv), potassium phosphate tribasic (10.51 g, 49.50 mmol, 3.0 equiv) and deionized $H_2O$ (10 mL) were added. The resulting mixture was stirred at 100° C. overnight. After completion of the reaction, the mixture was allowed to cool down to room temperature and the crude was filtered on celite. To the solution, deionized $H_2O$ (300 mL) and ethyl acetate (300 mL) were added. The layers were separated and the organic layer was washed with deionized $H_2O$ and brine (2×). The aqueous layer was extracted with dichloromethane (2×). The combined organic layers were concentrated under reduced pressure. Step 3. The above residue was dissolved in 1,4-dioxane (40 mL) and an aqueous solution of HCl (3 M, 40 mL) was added. The reaction mixture was stirred at 80° C. overnight. After completion of the reaction, the mixture was cool down to room temperature. Ethyl acetate (200 mL) and deionized $H_2O$ (200 mL) were added and the two layers were separated. The aqueous layer was washed with ethyl acetate (3×). The aqueous layer was basified to pH=10. The solid formed was filtered and washed with acetonitrile to obtain 4-(difluoromethyl)-5-(4-morpholino-6-(piperazin-1-yl)-1,3,5-triazin-2-yl)pyrimidin-2-amine as a beige solid (4.91 g, 12.48 mmol, 76%). MALDI-MS: m/z=394.205 $[M+H]^+$.

Method 3: tert-butyl 3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)azetidine-1-carboxylate

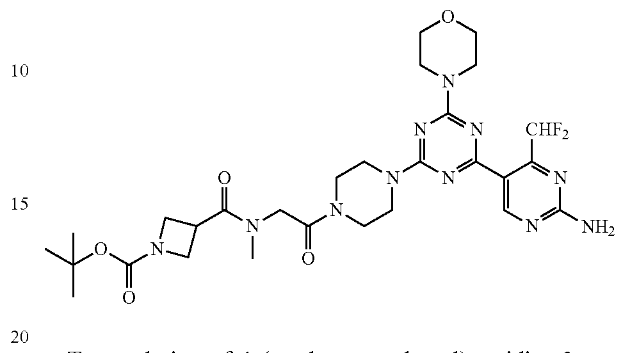

To a solution of 1-(tert-butoxycarbonyl)azetidine-3-carboxylic acid (581 mg, 2.89 mmol, 1.2 equiv) in anhydrous N,N-dimethylformamide (DMF, approx. 1 mL/0.18 mmol), O-(1H-6-chlorobenzotriazole-1-yl)-1,1,3,3-tetramethyluronium hexafluorophosphate (HCTU, 1.2 equiv) and N,N-diisopropylethylamine (3.2 equiv) were added at 0° C. under nitrogen atmosphere. The resulting mixture was stirred for 5 minutes at 0° C., then 2-(4-(4-(2-amino-4-(difluoromethyl)pyrimidin-5-yl)-6-morpholino-1,3,5-triazin-2-yl)piperazin-1-yl)-N-methyl-2-oxoethan-1-aminium chloride (or the respective HCl salt) was added and the reaction was stirred at room temperature for 4-16 hours. After completion of the reaction, DMF was removed under high vacuum. The crude was dissolved in DCM and the organic layer was washed with deionized $H_2O$ (2×) and an aqueous saturated $Na_2CO_3$-solution (3×). The organic layer was dried over $Na_2SO_4$, filtered and concentrated under reduced pressure. Purification by column chromatography on silica gel (dichloromethane/methanol/ammonia: 100:0:0→96:4:0.04) gave compound tert-butyl 3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)azetidine-1-carboxylate as a colorless solid (1.237 g, 1.91 mmol, 79%). MALDI-MS: m/z=648.7 $[M+H]^+$; m/z=548.4 $[(M-t\text{-}Butyl)+H]^+$.

Method 4: 3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)azetidin-1-ium chloride

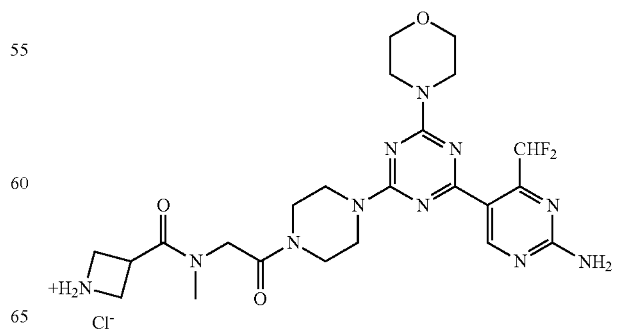

To a solution of the respective Boc-protected amine (1.0 equiv.) in THF (approx. 1 mL/0.10 mmol), a 4 M solution of HCl in dioxane (17 equiv.) was added dropwise. The mixture was stirred at room temperature for 16 hours. The mixture was reduced to dryness under reduced pressure. The product was precipitated from ACN, filtered and washed with cold ACN. The HCl salt of the product was used for the next step without further purification. 3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)azetidin-1-ium chloride was obtained as a colorless solid (987 mg, 1.69 mmol, 91%). MALDI-MS: m/z=548.4 $[M+H]^+$.

Preparation of Compounds of the Invention

General Procedure 1

To a solution of the respective carboxylic acid (1.0-1.5 equiv) in anhydrous N,N-dimethylformamide (DMF, approx. 1 mL/0.18 mmol), O-(1H-6-chlorobenzotriazole-1-yl)-1,1,3,3-tetramethyluronium hexafluorophosphate (HCTU, 1.1 equiv) and N,N-diisopropylethylamine (3.2 equiv) were added at 0° C. under nitrogen atmosphere. The resulting mixture was stirred for 5 minutes at 0° C., then the respective HCl salt (1.0 equiv) was added and the reaction was stirred at room temperature for 4-16 hours. After completion of the reaction, DMF was removed under high vacuum. The crude was dissolved in DCM and the organic layer was washed with deionized $H_2O$ (2×) and an aqueous saturated $Na_2CO_3$-solution (3×). The organic layer was dried over $Na_2SO_4$, filtered and concentrated under reduced pressure. The crude product was purified by column chromatography on silica gel and then recrystallized from dichloromethane/pentane.

Example 1

1-((R)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one

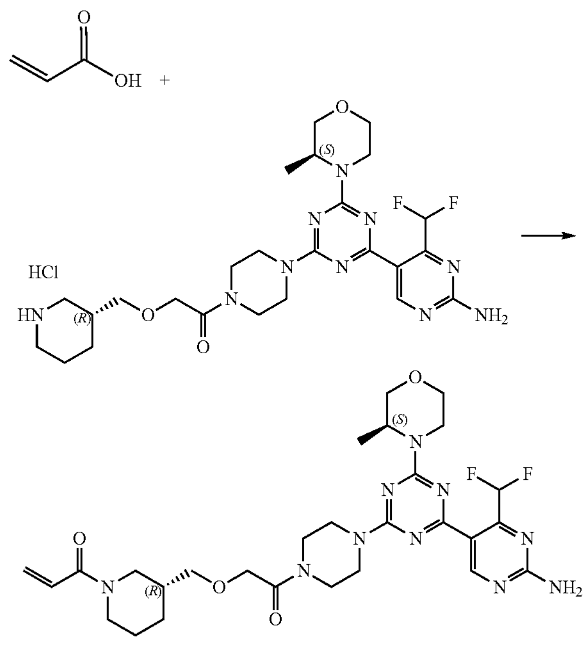

1-((R)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-yl)prop-2-en-1-one was prepared according to general procedure 1 from (R)-3-((2-(4-(4-(2-amino-4-(difluoromethyl)pyrimidin-5-yl)-6-((S)-3-methylmorpholino)-1,3,5-triazin-2-yl)piperazin-1-yl)-2-oxoethoxy)methyl)piperidin-1-ium chloride (193 mg, 0.32 mmol, 1.0 equiv) and acrylic acid (26 mg, 0.35 mmol, 1.1 equiv). Purification by column chromatography on silica gel (dichloromethane/methanol/ammonia: 100:0:0→96:4:0.04) gave the desired compound as a colorless solid (65 mg, 0.11 mmol, 33%). HRMS (m/z): $[M+Na]^+$ calc. for $C_{28}H_{38}F_2N_{10}NaO_4$, 639.2938; found: 639.2948. HPLC (acetonitrile with 0.1% TFA): $t_R$=7.20 min (98.9% purity).

Example 2

1-((R)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)piperidin-1-yl)prop-2-en-1-one

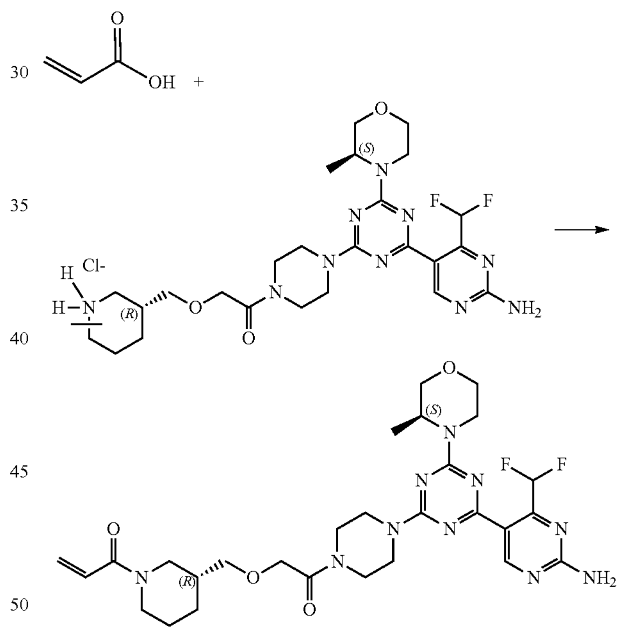

1-((R)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)piperidin-1-yl)prop-2-en-1-one was prepared according to general procedure 1 from (R)-3-(3-(4-(4-(2-amino-4-(difluoromethyl)pyrimidin-5-yl)-6-((S)-3-methylmorpholino)-1,3,5-triazin-2-yl)piperazin-1-yl)-3-oxopropoxy)piperidin-1-ium chloride (150 mg, 0.25 mmol, 1.0 equiv) and acrylic acid (20 mg, 0.27 mmol, 1.1 equiv). Purification by column chromatography on silica gel (dichloromethane/methanol/ammonia: 100:0:0→97:3:0.03) gave the desired compound as a colorless solid (32 mg, 0.052 mmol, 20%). HRMS (m/z): $[M+Na]^+$ calc. for $C_{28}H_{38}F_2N_{10}NaO_4$, 639.2938; found: 639.2947. HPLC: $t_R$=7.08 min (>99.9% purity).

Example 3

(R,Z)-2-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidine-1-carbonyl)-3-cyclopropylacrylonitrile

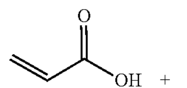

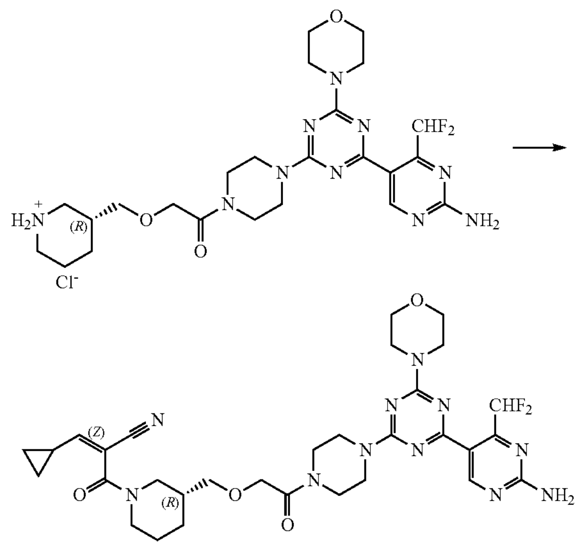

(R,Z)-2-(3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidine-1-carbonyl)-3-cyclopropylacrylonitrile was prepared according to general procedure 1 from (R)-3-((2-(4-(4-(2-amino-4-(difluoromethyl)pyrimidin-5-yl)-6-morpholino-1,3,5-triazin-2-yl)piperazin-1-yl)-2-oxoethoxy)methyl)piperidin-1-ium chloride (226 mg, 0.39 mmol, 1.0 equiv.) and (Z)-2-cyano-3-cyclopropylacrylic acid (118 mg, 0.85 mmol, 2.2 equiv.). Purification by column chromatography on silica gel (dichloromethane/methanol/ammonia: 100:0:0→92:8:0.08) gave the desired compound as a colorless solid (148 mg, 0.22 mmol, 57%).

HRMS (m/z): $[M+Na]^+$ calc. for $C_{31}H_{39}F_2N_{11}NaO_4$ 690.3047; found: 690.3052. HPLC: $t_R$=7.50 min (96.7% purity).

Example 4

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-3-carboxamide

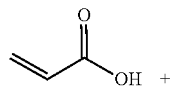

-continued

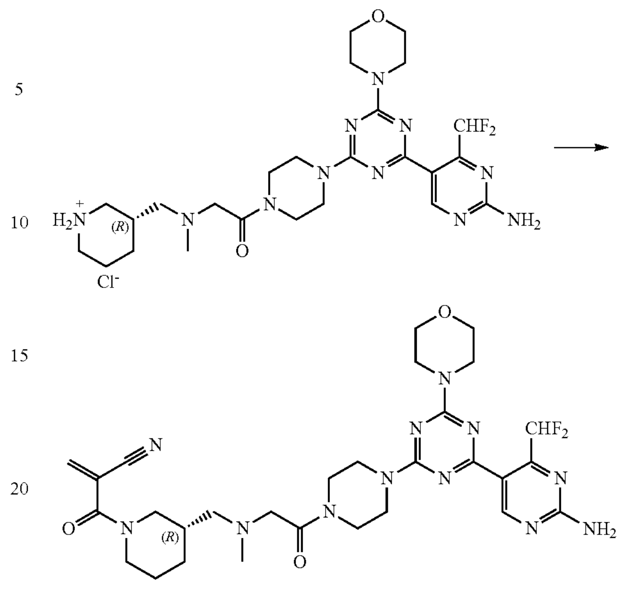

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylpiperidine-3-carboxamide was prepared according to general procedure 1 from (R)-3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)piperidin-1-ium chloride (1.139 g, 1.86 mmol, 1.0 equiv) and acrylic acid (147 mg, 2.05 mmol, 1.1 equiv). Purification by column chromatography on silica gel (dichloromethane/methanol/ammonia: 100:0:0→97:3:0.03) gave the desired compound as a colorless solid (305 mg, 0.48 mmol, 26%). HRMS (m/z): $[M+Na]^+$ calc. for $C_{28}H_{37}F_2N_{11}NaO_4$, 652.2890; found: 652.2893. HPLC: $t_R$=6.20 min (98.3% purity).

Example 5

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-3-carboxamide

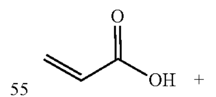

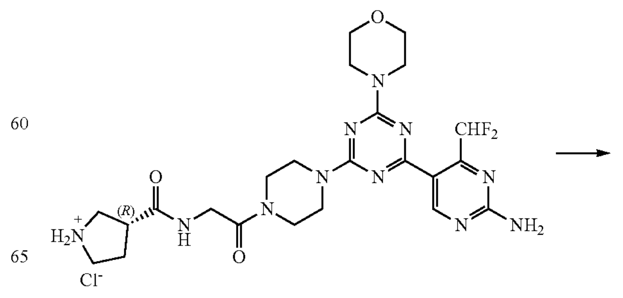

-continued

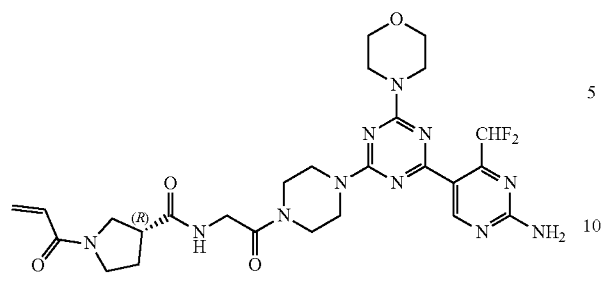

(R)-1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)pyrrolidine-3-carboxamide was prepared according to general procedure 1 from (R)-3-((2-(4-(4-(2-amino-4-(difluoromethyl)pyrimidin-5-yl)-6-morpholino-1,3,5-triazin-2-yl)piperazin-1-yl)-2-oxoethyl)carbamoyl)pyrrolidin-1-ium chloride (274 mg, 0.47 mmol, 1.0 equiv) and acrylic acid (37 mg, 0.52 mmol, 1.1 equiv). Purification by column chromatography on silica gel (dichloromethane/methanol/ammonia: 100:0:0→96:4:0.04) gave the desired compound as a colorless solid (134 mg, 0.22 mmol, 47%). HRMS (m/z): $[M+Na]^+$ calc. for $C_{26}H_{33}F_2N_{11}NaO_4$, 624.2577; found: 624.2581. HPLC: $t_R$=5.84 min (98.4% purity).

Example 6

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylazetidine-3-carboxamide

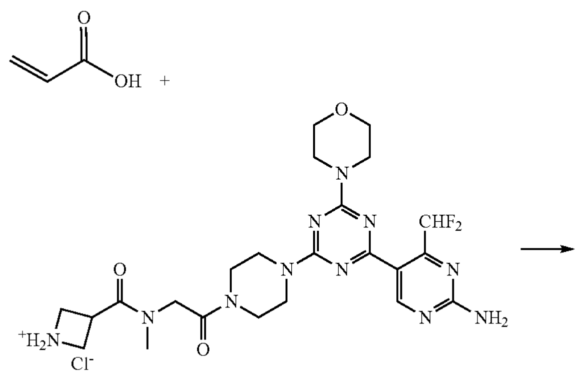

-continued

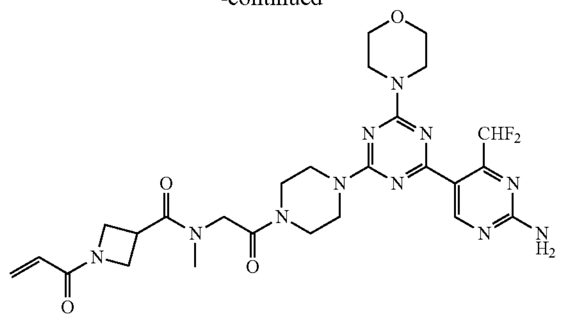

1-acryloyl-N-(2-(4-(4-(2-amino-4-(difluoromethyl)pyrimidin-5-yl)-6-morpholino-1,3,5-triazin-2-yl)piperazin-1-yl)-2-oxoethyl)-N-methylazetidine-3-carboxamide was prepared according to general procedure 1 from 3-((2-(4-(4-(2-amino-4-(difluoromethyl)pyrimidin-5-yl)-6-morpholino-1,3,5-triazin-2-yl)piperazin-1-yl)-2-oxoethyl)(methyl)carbamoyl)azetidin-1-ium chloride (946 mg, 1.62 mmol, 1.0 equiv) and acrylic acid (128 mg, 1.78 mmol, 1.1 equiv). Purification by column chromatography on silica gel (dichloromethane/methanol/ammonia: 100:0:0→96:4:0.04) gave the desired compound as a colorless solid (358 mg, 0.60 mmol, 37%). HRMS (m/z): $[M+Na]^+$ calc. for $C_{26}H_{33}F_2N_{11}NaO_4$, 624.2577; found: 624.2579. HPLC: $t_R$=5.81 min (98.4% purity).

Determination of Inhibitor Apparent Dissociation Constant

Apparent dissociation constants of compounds [$K_{i(app)}$] for p110α were determined by LanthaScreen Technology (Life Technologies), as described in Ref.[21].

Determination of Kinetic Constants

Maximum potential rate of covalent bond formation ($K_{inact}$) and dissociation constant of the first reversible binding ($K_i$) of compounds for p110α were determined by LanthaScreen Technology (Life Technologies). The calculation of kinetic parameters was carried out through global fitting for numerical integration by using KinTek Global Kinetic Explorer modelling software[22-27].

In Cell Western Cellular PI3K Signaling and $IC_{50}$ Determination

Protein phosphorylation was detected as follows: pSer473 of PKB/Akt with rabbit polyclonal antibody from Cell Signaling Technology (CST) (#4058) by In-Cell Western assays, where $1.2\times10^4$ SKOV3 cells/well in 96-well plates were plated (Cell Carrier, PerkinElmer) for 24 hours (37° C., 5% $CO_2$), as described in Ref.[21].

NanoBRET Target Engagement Assays

N-terminal NanoLuc fused PI3K were encoded in pFN31K expression vector (Promega), including flexible Gly-Ser-Ser-Gly-Ala-Ile-Ala linkers between NanoLuc and each full-length of target kinases including PI3Kα, PI3Kα C862S, PI3Kβ, and PI3Kδ. HEK293 cells were co-transfected with NanoLuc/PI3K and its regulatory subunit p85 at a mass ratio 1:10 using jetPEI transfection reagent (Polyplus transfection, #101B-010N).

TABLE 1

Intrinsic reactivity and in vitro data for some of the compounds of the invention and CNX-1351.

| Comp. | clogP[a] | $k_{chem}$, $[M^{-1} \cdot s^{-1}]^b$ | $SD | $k_{inact}$ PI3Kα, $[s^{-1}]$ | $SD | $K_i$ PI3Kα, [nM] | SD | $k_{inact}/K_i$, $[nM^{-1} \cdot s^{-1}]$ | SD |
|---|---|---|---|---|---|---|---|---|---|
| CNX-1351 | 4.68 | $2.22 \times 10^{-4}$ | $4.05 \times 10^{-5}$ | $6.57 \times 10^{-4}$ | $4.05 \times 10^{-5}$ | 38.09 | 3.18 | $1.74 \times 10^{-5}$ | $2.08 \times 10^{-6}$ |
| 1 | — | — | — | $4.19 \times 10^{-4}$ | $6.06 \times 10^{-5}$ | 2.70 | 0.26 | $1.56 \times 10^{-4}$ | $3.13 \times 10^{-5}$ |
| 2 | — | — | — | $2.62 \times 10^{-4}$ | $3.19 \times 10^{-5}$ | 2.78 | 0.26 | $9.43 \times 10^{-5}$ | $2.98 \times 10^{-6}$ |
| 3 | — | — | — | $4.32 \times 10^{-4}$ | $7.21 \times 10^{-5}$ | 8.72 | 1.22 | 5.02 × 10–4 | $8.44 \times 10^{-5}$ |

TABLE 1-continued

Intrinsic reactivity and in vitro data for some of the compounds of the invention and CNX-1351.

| Comp. | clogP[a] | $k_{chem}$, $[M^{-1} \cdot s^{-1}]$[b] | $SD | $k_{inact}$ PI3Kα, $[s^{-1}]$ | $SD | $K_i$ PI3Kα, [nM] | SD | $k_{inact}/K_i$, $[nM^{-1} \cdot s^{-1}]$ | SD |
|---|---|---|---|---|---|---|---|---|---|
| 4 | — | — | — | $3.83 \times 10^{-3}$ | $6.55 \times 10^{-5}$ | 11.7 | 0.25 | $3.25 \times 10^{-4}$ | $1.03 \times 10^{-5}$ |
| 5 | — | — | — | $5.20 \times 10^{-3}$ | $2.66 \times 10^{-4}$ | 8.88 | 1.26 | $5.95 \times 10^{-4}$ | $1.06 \times 10^{-4}$ |
| 6 | — | — | — | — | — | — | — | — | — |
| 7 | — | — | — | — | — | — | — | — | — |
| 8 | — | — | — | $1.10 \times 10^{-2}$ | $3.60 \times 10^{-4}$ | 2.78 | 0.14 | $3.96 \times 10^{-3}$ | $3.25 \times 10^{-4}$ |
| 9 | | | | $1.05 \times 10^{-2}$ | $4.16 \times 10^{-4}$ | 1.11 | 0.05 | $9.43 \times 10^{-3}$ | $2.13 \times 10^{-4}$ |
| 10 | | | | $1.11 \times 10^{-2}$ | $2.64 \times 10^{-4}$ | 1.09 | 0.07 | $1.02 \times 10^{-2}$ | $8.70 \times 10^{-4}$ |
| 11 | | | | N/A | N/A | 1.85 | 0.28 | N/A | N/A |
| 12 | | | | — | — | — | — | — | — |
| 13 | | | | — | — | — | — | — | — |
| 14 | | | | N/A | N/A | 1.91 | 0.29 | N/A | N/A |
| 15 | 0.79 | $0.73 \times 10^{-3}$ | $3.73 \times 10^{-5}$ | $5.47 \times 10^{-4}$ | $2.43 \times 10^{-5}$ | 3.63 | 0.42 | $1.51 \times 10^{-4}$ | $1.16 \times 10^{-5}$ |
| 16 | 0.79 | $0.76 \times 10^{-3}$ | $5.03 \times 10^{-5}$ | $3.56 \times 10^{-3}$ | $2.76 \times 10^{-4}$ | 3.89 | 0.10 | $9.14 \times 10^{-4}$ | $9.59 \times 10^{-5}$ |
| 17 | 1.04 | $0.68 \times 10^{-3}$ | $1.58 \times 10^{-5}$ | $2.51 \times 10^{-4}$ | $2.97 \times 10^{-5}$ | 7.66 | 0.06 | $3.27 \times 10^{-5}$ | $4.12 \times 10^{-6}$ |
| 18 | 1.04 | $0.704 \times 10^{-3}$ | $1.02 \times 10^{-5}$ | $4.33 \times 10^{-3}$ | $3.15 \times 10^{-4}$ | 6.08 | 0.10 | $7.11 \times 10^{-4}$ | $6.44 \times 10^{-5}$ |
| 19 | 1.60 | — | — | $1.96 \times 10^{-4}$ | $1.21 \times 10^{-5}$ | 12.0 | 0.27 | $1.63 \times 10^{-5}$ | $1.37 \times 10^{-6}$ |
| 20 | 1.05 | $4.44 \times 10^{-3}$ | $1.36 \times 10^{-4}$ | $6.50 \times 10^{-4}$ | $2.65 \times 10^{-5}$ | 3.06 | 0.10 | $2.12 \times 10^{-4}$ | $5.59 \times 10^{-6}$ |
| 21 | 1.05 | $4.69 \times 10^{-3}$ | $2.02 \times 10^{-4}$ | $8.75 \times 10^{-4}$ | $3.06 \times 10^{-5}$ | 3.85 | 0.21 | $2.27 \times 10^{-4}$ | $1.86 \times 10^{-5}$ |
| 22 | 1.30 | $0.94 \times 10^{-3}$ | $1.55 \times 10^{-5}$ | $3.09 \times 10^{-4}$ | $4.00 \times 10^{-6}$ | 5.74 | 0.49 | $5.40 \times 10^{-5}$ | $5.41 \times 10^{-6}$ |
| 23 | 1.30 | $1.00 \times 10^{-3}$ | $2.06 \times 10^{-5}$ | $2.31 \times 10^{-4}$ | $1.90 \times 10^{-5}$ | 8.47 | 0.19 | $2.72 \times 10^{-5}$ | $2.31 \times 10^{-6}$ |
| 24 | 0.40 | $0.59 \times 10^{-3}$ | $1.18 \times 10^{-5}$ | $2.60 \times 10^{-3}$ | $3.24 \times 10^{-4}$ | 8.34 | 0.13 | $3.11 \times 10^{-4}$ | $3.37 \times 10^{-5}$ |
| 25 | 0.40 | $0.62 \times 10^{-3}$ | $1.60 \times 10^{-5}$ | $5.14 \times 10^{-3}$ | $1.50 \times 10^{-4}$ | 5.36 | 0.26 | $9.61 \times 10^{-4}$ | $6.89 \times 10^{-5}$ |
| 26 | 0.64 | $0.50 \times 10^{-3}$ | $1.79 \times 10^{-5}$ | $7.89 \times 10^{-4}$ | $3.20 \times 10^{-5}$ | 5.28 | 0.69 | $1.50 \times 10^{-4}$ | $1.62 \times 10^{-5}$ |
| 27 | 0.64 | $0.49 \times 10^{-3}$ | $9.27 \times 10^{-6}$ | $3.20 \times 10^{-3}$ | $1.59 \times 10^{-4}$ | 6.07 | 0.47 | $5.31 \times 10^{-4}$ | $6.49 \times 10^{-5}$ |
| 28 | 0.66 | $6.55 \times 10^{-3}$ | $1.94 \times 10^{-4}$ | $2.81 \times 10^{-4}$ | $1.95 \times 10^{-5}$ | 6.32 | 0.38 | $4.45 \times 10^{-5}$ | $2.24 \times 10^{-6}$ |
| 29 | 0.66 | $7.90 \times 10^{-3}$ | $2.39 \times 10^{-4}$ | $2.75 \times 10^{-4}$ | $5.19 \times 10^{-6}$ | 6.74 | 0.09 | $4.07 \times 10^{-5}$ | $1.33 \times 10^{-6}$ |
| 30 | 0.90 | $0.58 \times 10^{-3}$ | $2.02 \times 10^{-5}$ | — | — | — | — | — | — |
| 31 | 0.90 | $0.52 \times 10^{-3}$ | $0.52 \times 10^{-5}$ | — | — | — | — | — | — |
| 32 | 0.14 | $5.17 \times 10^{-3}$ | $2.35 \times 10^{-4}$ | — | — | — | — | — | — |
| 33 | 0.39 | $5.81 \times 10^{-3}$ | $2.51 \times 10^{-4}$ | $7.57 \times 10^{-3}$ | $4.90 \times 10^{-4}$ | 6.43 | 0.22 | $1.17 \times 10^{-3}$ | $1.05 \times 10^{-4}$ |
| 34 | 0.74 | — | — | — | — | — | — | — | — |
| 35 | — | $6.62 \times 10^{-3}$ | $4.39 \times 10^{-5}$ | $1.69 \times 10^{-3}$ | $1.85 \times 10^{-4}$ | 13.4 | 1.13 | $1.26 \times 10^{-4}$ | $1.27 \times 10^{-5}$ |
| 36 | 0.95 | — | — | — | — | — | — | — | — |
| 37 | 0.57 | $6.36 \times 10^{-3}$ | $1.33 \times 10^{-4}$ | — | — | — | — | — | — |
| 44 | 0.65 | $3.70 \times 10^{-4}$ | $1.28 \times 10^{-5}$ | $1.20 \times 10^{-3}$ | $2.52 \times 10^{-5}$ | 2.94 | 0.38 | 4.14 × 10–4 | $4.99 \times 10^{-5}$ |
| 45 | 0.89 | $3.54 \times 10^{-4}$ | $5.93 \times 10^{-6}$ | $1.08 \times 10^{-3}$ | $1.06 \times 10^{-4}$ | 5.15 | 0.18 | $2.10 \times 10^{-4}$ | $1.97 \times 10^{-5}$ |
| 46 | 1.47 | $2.90 \times 10^{-4}$ | $1.41 \times 10^{-5}$ | $1.02 \times 10^{-3}$ | $2.08 \times 10^{-5}$ | 4.29 | 0.29 | $2.39 \times 10^{-4}$ | $1.60 \times 10^{-5}$ |
| 47 | 2.68 | $2.25 \times 10^{-4}$ | $2.44 \times 10^{-6}$ | $5.04 \times 10^{-4}$ | $8.60 \times 10^{-5}$ | 7.15 | 0.59 | $7.03 \times 10^{-5}$ | $9.31 \times 10^{-6}$ |
| 40 | 1.19 | — | — | $1.63 \times 10^{-3}$ | $1.15 \times 10^{-5}$ | 7.27 | 0.16 | $2.24 \times 10^{-4}$ | $4.44 \times 10^{-6}$ |
| 41 | 1.61 | — | — | $1.21 \times 10^{-2}$ | $3.78 \times 10^{-4}$ | 11.55 | 0.74 | $1.05 \times 10^{-3}$ | $5.82 \times 10^{-5}$ |
| 42 | 1.19 | — | — | $5.37 \times 10^{-4}$ | $6.97 \times 10^{-5}$ | 7.10 | 0.41 | $7.54 \times 10^{-5}$ | $5.63 \times 10^{-6}$ |
| 43 | 1.61 | — | — | $1.43 \times 10^{-2}$ | $4.35 \times 10^{-4}$ | 13.76 | 0.48 | $1.04 \times 10^{-3}$ | $3.65 \times 10^{-5}$ |

[a]Marvin/JChem 20.9 was used for calculation of logP (partition coefficient).
[b]Intrinsic reactivity of the inhibitors measured with HPLC (1 mM inhibitor + 600 mM βME; n = 3).
[$]each mean and SD were calculated from 3 independent measurements.

TABLE 2

Cellular data for some of the compounds of the invention and CNX-1351.

| Comp. | $IC_{50}$ pPKB (S473) SKOV3, [nM] | $SD |
|---|---|---|
| CNX-1351 | 164 | 18 |
| 1 | 25.4 | 2.2 |
| 2 | 28.8 | 2.6 |
| 3 | 23.0 | 0.8 |
| 4 | 35.7 | 0.4 |
| 5 | 17.1 | 1.2 |
| 6 | — | — |
| 7 | — | — |
| 8 | 11.6 | 0.8 |
| 9 | 14.4 | 3.9 |
| 10 | 23.1 | 3.5 |
| 11 | 19.9 | 0.7 |
| 12 | 15.4 | 1.7 |
| 13 | 18.0 | 1.2 |
| 14 | 22.2 | 3.9 |
| 15 | 133 | 21 |

TABLE 2-continued

Cellular data for some of the compounds of the invention and CNX-1351.

| Comp. | $IC_{50}$ pPKB (S473) SKOV3, [nM] | $SD |
|---|---|---|
| 16 | 27.5 | 2.8 |
| 17 | 85.7 | 12 |
| 18 | 15.3 | 5.0 |
| 19 | 28.8 | 2.8 |
| 20 | 59.3 | 18.8 |
| 21 | 89.8 | 17.6 |
| 22 | 29.3 | 3.3 |
| 23 | 60.5 | 10.0 |
| 24 | 94.0 | 7.1 |
| 25 | 42.0 | 3.4 |
| 26 | 227 | 2.6 |
| 27 | 64.1 | 8.6 |
| 28 | 301 | 37 |
| 29 | 204 | 41 |
| 30 | — | — |
| 31 | 447 | 19 |

TABLE 2-continued

Cellular data for some of the compounds of the invention and CNX-1351.

| Comp. | $IC_{50}$ pPKB (S473) SKOV3, [nM] | $SD |
|---|---|---|
| 32 | 175 | 32 |
| 33 | 55.0 | 1.13 |
| 34 | 236 | 50 |
| 35 | 609 | 19 |
| 36 | 48.2 | 2.6 |
| 37 | 196 | 16 |
| 44 | 82 | 2.7 |
| 45 | 86 | 2.9 |
| 46 | 23 | 2.5 |
| 47 | 24 | 1.5 |

$each mean and SD were calculated from 2 or 3 independent measurements.

REFERENCES

21. Bohnacker, T.; Prota, A. E.; Beaufils, F.; Burke, J. E.; Melone, A.; Inglis, A. J.; Rageot, D.; Sele, A. M.; Cmiljanovic, V.; Cmiljanovic, N.; Bargsten, K.; Aher, A.; Akhmanova, A.; Diaz, J. F.; Fabbro, D.; Zvelebil, M.; Williams, R. L.; Steinmetz, M. O.; Wymann, M. P., Deconvolution of Buparlisib's mechanism of action defines specific PI3K and tubulin inhibitors for therapeutic intervention. *Nat Commun* 2017, 8, 14683.

22. Choi, B.; Rempala, G. A.; Kim, J. K., Beyond the Michaelis-Menten equation: Accurate and efficient estimation of enzyme kinetic parameters. *Sci Rep* 2017, 7 (1), 17018.

23. Janes, M. R.; Zhang, J.; Li, L. S.; Hansen, R.; Peters, U.; Guo, X.; Chen, Y.; Babbar, A.; Firdaus, S. J.; Darjania, L.; Feng, J.; Chen, J. H.; Li, S.; Li, S.; Long, Y. O.; Thach, C.; Liu, Y.; Zarieh, A.; Ely, T.; Kucharski, J. M.; Kessler, L. V.; Wu, T.; Yu, K.; Wang, Y.; Yao, Y.; Deng, X.; Zarrinkar, P. P.; Brehmer, D.; Dhanak, D.; Lorenzi, M. V.; Hu-Lowe, D.; Patricelli, M. P.; Ren, P.; Liu, Y., Targeting KRAS Mutant Cancers with a Covalent G12C-Specific Inhibitor. *Cell* 2018, 172 (3), 578-589. e17.

24. Johnson, K. A., Fitting enzyme kinetic data with KinTek Global Kinetic Explorer. *Methods Enzymol* 2009, 467, 601-626.

25. Müller, M. P.; Jeganathan, S.; Heidrich, A.; Campos, J.; Goody, R. S., Nucleotide based covalent inhibitors of KRas can only be efficient in vivo if they bind reversibly with GTP-like affinity. *Sci Rep* 2017, 7 (1), 3687.

26. Schwartz, P. A.; Kuzmic, P.; Solowiej, J.; Bergqvist, S.; Bolanos, B.; Almaden, C.; Nagata, A.; Ryan, K.; Feng, J.; Dalvie, D.; Kath, J. C.; Xu, M.; Wani, R.; Murray, B. W., Covalent EGFR inhibitor analysis reveals importance of reversible interactions to potency and mechanisms of drug resistance. *Proc Natl Acad Sci U S A* 2014, 111 (1), 173-8.

27. Johnson, K. A.; Simpson, Z. B.; Blom, T., Global kinetic explorer: a new computer program for dynamic simulation and fitting of kinetic data. *Anal Biochem* 2009, 387 (1), 20-9.

The invention claimed is:

1. A compound of formula (IV), or a pharmaceutically acceptable salt thereof, (IV)

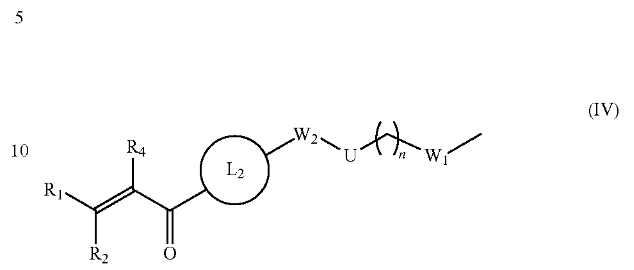

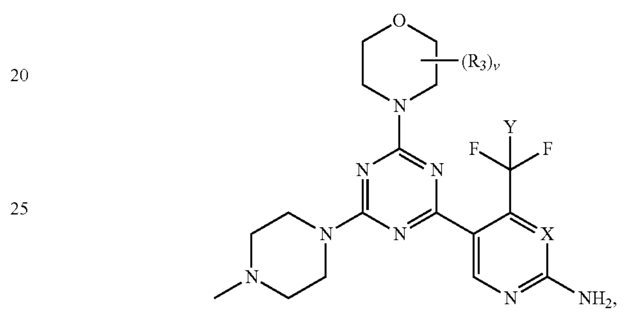

wherein

X is CH or N,

Y is H or F, $R_1$ and $R_2$ are independently of each other selected from H, $CH_3$, cyclopropyl, —F, —$CH_2$—F, —$CH_2$—$CH_2$—F, —CN,

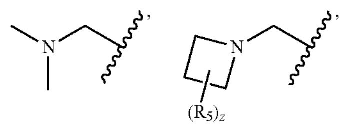

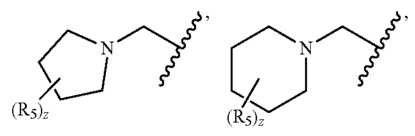

and,

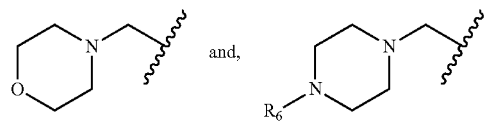

with $R_5$ being F or $CH_3$, $R_6$ being $C_{1-6}$-alkyl and z being 0, 1 or 2, $R_3$ is $C_{1-3}$-alkyl or two residues $R_3$ form a bridge —$(CH_2)_r$— with r being 1, 2 or 3, v is 0, 1, 2, 3 or 4, $R_4$ is H, F or —CN, $L_2$ is a moiety selected from

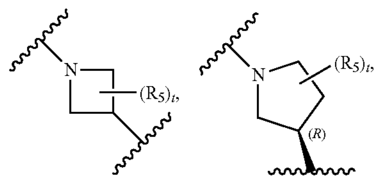

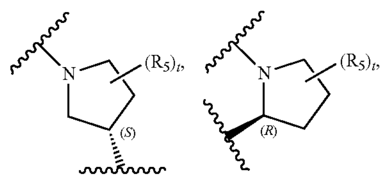

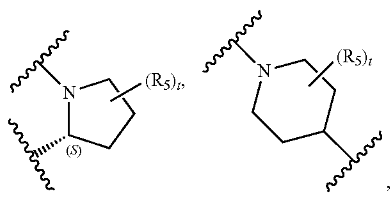

,

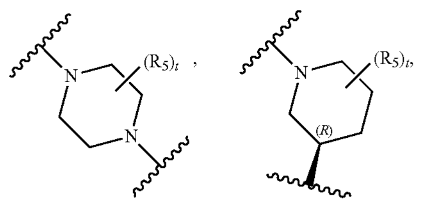

,

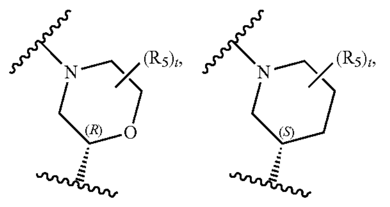

-continued

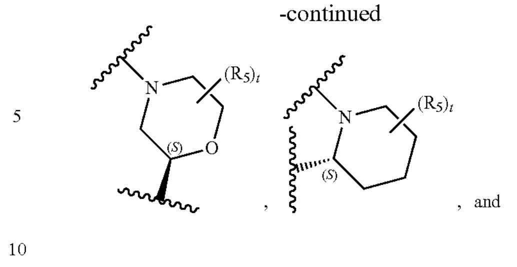

, , and

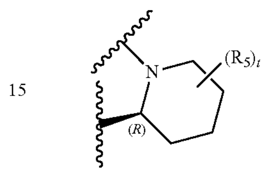

with $R_5$ being $C_{1-3}$-alkyl, F, —$CH_2CN$ or —CN and t being 0, 1 or 2, $W_1$ is CO or $CH_2$, $W_2$ is selected from O, $CH_2$ and CO, U is selected from O, $CH_2$, CO, NH, and $N(CH_3)$, n is 1 or 2.

2. The compound according to claim 1, wherein $R_1$ is H, $CH_3$ or —$CH_2F$.

3. The compound according to claim 1, wherein $R_2$ is H or cyclopropyl.

4. The compound according to claim 1, wherein $R_2$ is cyclopropyl and $R_4$ is —CN.

5. The compound according to claim 1, wherein $R_3$ is a $C_{1-3}$-alkyl.

6. The compound according to claim 1, wherein v is 0, 1 or 2.

7. The compound according to claim 1, wherein U is selected from O, $CH_2$, NH and $N(CH_3)$.

8. The compound according to claim 1, wherein the compound is a compound of formula (V), (V)

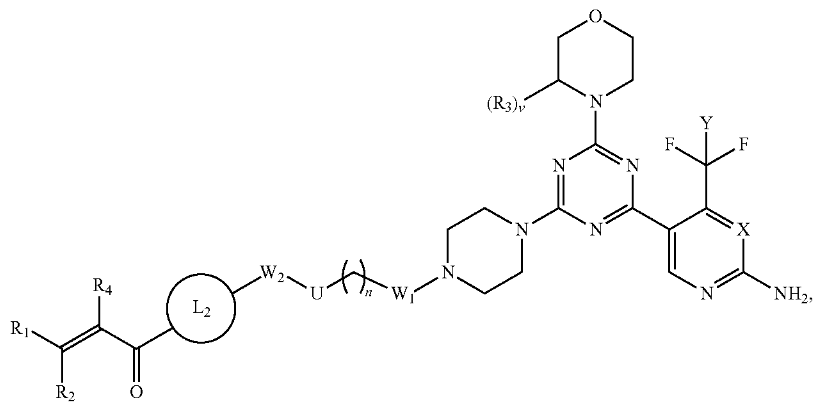

wherein $R_1$, $R_2$, $R_3$, $R_4$, $W_1$, n, U, $W_2$, $L_2$ are defined as described above, $R_1$ and $R_2$ are independently of each other selected from H, $CH_3$, cyclopropyl, —F, —$CH_2$—F, —$CH_2$—$CH_2$—F, —CN,

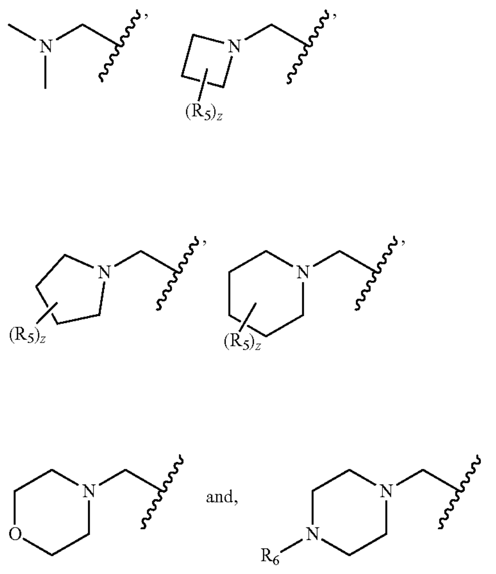

and, with $R_5$ being For $CH_3$, $R_6$ being $C_{1-6}$-alkyl and z being 0, 1 or 2, $R_3$ is $C_{1-3}$-alkyl or two residues $R_3$ form a bridge —$(CH_2)_r$— with r being 1, 2 or 3, $R_4$ is H, F or —CN, $L_2$ is a moiety selected from

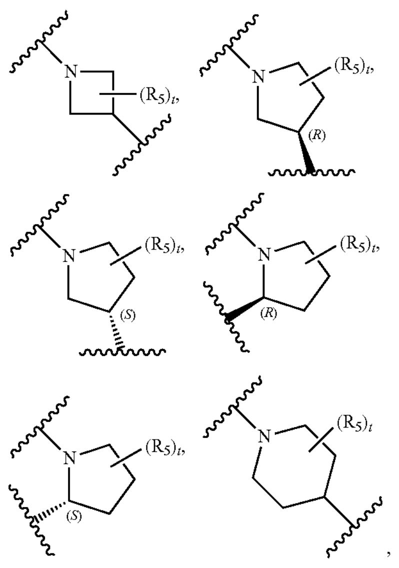

,

-continued

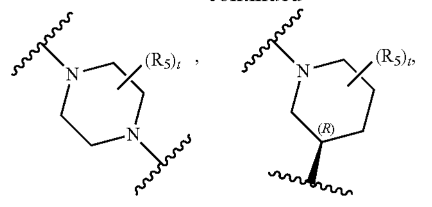

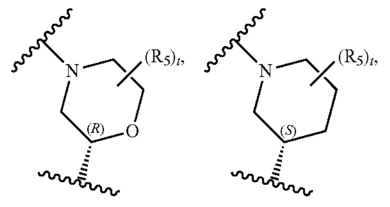

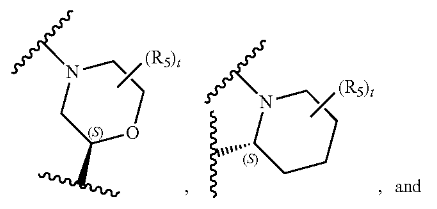

, and

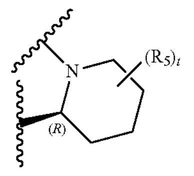

with $R_5$ being $C_{1-3}$-alkyl, F, —$CH_2$CN or —CN and t being 0, 1 or 2, $W_1$ is CO or $CH_2$, $W_2$ is selected from O, $CH_2$ and CO, U is selected from O, $CH_2$, CO, NH, and $N(CH_3)$, n is 1 or 2 v is 0 or 1.

9. A method for treatment of a disease caused by an activating mutation of the PI3KCA gene or activation of a class I PI3K, the method comprising administering the compound according to claim 1 to a patient in need thereof, thereby treating the disease.

10. The method according to claim 9, wherein the disease is caused by an activating mutation of PI3Kα.

11. The method for treatment according to claim 9, wherein the disease is a tumor disease, overgrowth syndrome, neurological disease disorder, or immunological disease disorder.

12. The method according to claim 11, wherein the tumor is a solid tumor.

13. The method according to claim 11, wherein the tumor disease is selected from lymphoma and leukemia.

14. The compound of claim 1, wherein the compound is of formula (IVa)
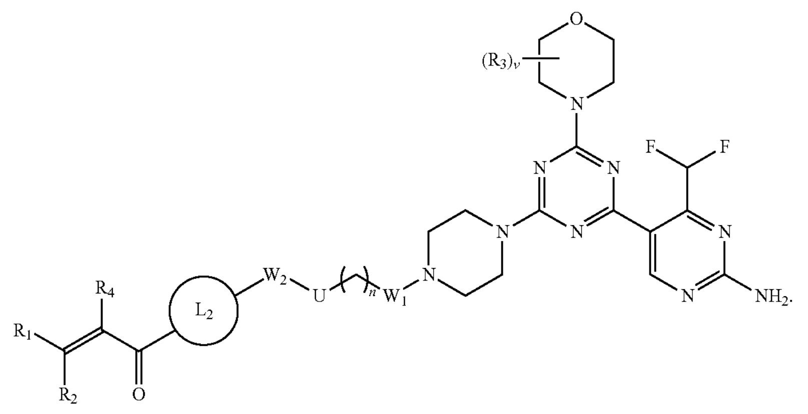
15. The compound of claim 8, wherein the compound is of formula (Va)
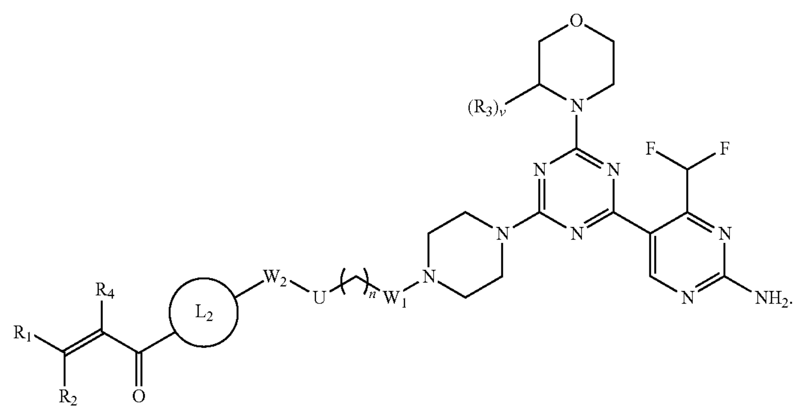
* * * * *